United States Patent
Old et al.

(10) Patent No.: US 7,879,854 B2
(45) Date of Patent: *Feb. 1, 2011

(54) SUBSTITUTED GAMMA LACTAMS AS THERAPEUTIC AGENTS

(75) Inventors: David W. Old, Irvine, CA (US); Danny T. Dinh, Garden Grove, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/427,911

(22) Filed: Apr. 22, 2009

(65) Prior Publication Data

US 2009/0286787 A1 Nov. 19, 2009

Related U.S. Application Data

(60) Provisional application No. 61/047,510, filed on Apr. 24, 2008.

(51) Int. Cl.
| | |
|---|---|
| C07D 413/12 | (2006.01) |
| C07D 413/06 | (2006.01) |
| C07D 417/06 | (2006.01) |
| C07D 417/12 | (2006.01) |
| C07D 405/12 | (2006.01) |
| C07D 405/06 | (2006.01) |
| C07D 207/12 | (2006.01) |
| A61K 31/422 | (2006.01) |
| A61K 31/421 | (2006.01) |
| A61K 31/427 | (2006.01) |
| A61K 31/4025 | (2006.01) |
| A61K 31/4015 | (2006.01) |

(52) U.S. Cl. .............. 514/237.2; 544/141; 548/527; 548/551; 548/517; 548/186; 548/204; 548/236; 514/365; 514/369; 514/374; 514/376; 514/422

(58) Field of Classification Search .......... None
See application file for complete search history.

(56) References Cited

U.S. PATENT DOCUMENTS

| | | | |
|---|---|---|---|
| 4,166,452 | A | 9/1979 | Generales, Jr. |
| 4,256,108 | A | 3/1981 | Theeuwes |
| 4,265,874 | A | 5/1981 | Bonsen et al. |
| 6,437,146 | B1 | 8/2002 | Hattori et al. |
| 6,710,072 | B2 | 3/2004 | Burk et al. |
| 2009/0270392 | A1* | 10/2009 | Old et al. .......... 514/235.5 |

OTHER PUBLICATIONS

U.S. Appl. No. 12/427,968, filed Apr. 2009, Old et al.*
U.S. Appl. No. 60/660,748, filed Mar. 10, 2005, David W. Old.
U.S. Appl. No. 61/022,172, filed Jan. 18, 2008, David W. Old.
Remington's Pharmaceutical Sciences, Mack Publishing Company, Easton, Pa., 16th Edition, 1980.
Chourasia and Jain in J Pharm Pharmaceut Sci 6 (1): 33-66, 2003.
Shareef et. al (AAPS PharmSci 2003; 5 (2) Article 17).

* cited by examiner

*Primary Examiner*—Yong Chu
*Assistant Examiner*—Michael Barker
(74) *Attorney, Agent, or Firm*—Doina G. Ene; John E. Wurst; Kevin J. Forrestal

(57) ABSTRACT

A compound comprising

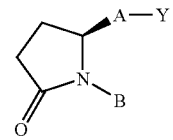

or a pharmaceutically acceptable salt thereof, or a prodrug thereof is disclosed herein. Y, A, and B are as described herein.

Methods, compositions, and medicaments related to these compounds are also disclosed.

15 Claims, No Drawings

US 7,879,854 B2

SUBSTITUTED GAMMA LACTAMS AS THERAPEUTIC AGENTS

RELATED APPLICATION

This application claims the benefit of U.S. Provisional Application Ser. No. 61/047,510, filed Apr. 24, 2008, the disclosure of which is hereby incorporated in its entirety herein by reference

DESCRIPTION OF RELATED ART

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

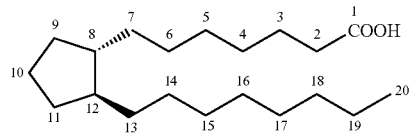

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

Prostaglandin $EP_2$ selective agonists are believed to have several medical uses. For example, U.S. Pat. No. 6,437,146 teaches the use of prostaglandin $EP_2$ selective agonists "for treating or preventing inflammation and pain in joint and muscle (e.g., rheumatoid arthritis, rheumatoid spondylitis, osteoarthritis, gouty arthritis, juvenile arthritis, etc.), inflammatory skin condition (e.g., sunburn, burns, eczema, dermatitis, etc.), inflammatory eye condition (e.g., conjunctivitis, etc.), lung disorder in which inflammation is involved (e.g., asthma, bronchitis, pigeon fancier's disease, farmer's lung, etc.), condition of the gastrointestinal tract associated with inflammation (e.g., aphthous ulcer, Chrohn's disease, atrophic gastritis, gastritis varialoforme, ulcerative colitis, coeliac disease, regional ileitis, irritable bowel syndrome, etc.), gingivitis, inflammation, pain and tumescence after operation or injury, pyrexia, pain and other conditions associated with inflammation, allergic disease, systemic lupus crythematosus, scleroderma, polymyositis, tendinitis, bursitis, periarteritis nodose, rheumatic fever, Sjgren's syndrome, Behcet disease, thyroiditis, type I diabetes, diabetic complication (diabetic microangiopathy, diabetic retinopathy, diabetic nephropathy, etc.), nephrotic syndrome, aplastic anemia, myasthenia gravis, uveitis contact dermatitis, psoriasis, Kawasaki disease, sarcoidosis, Hodgkin's disease, Alzheimers disease, kidney dysfunction (nephritis, nephritic syndrome, etc.), liver dysfunction (hepatitis, cirrhosis, etc.), gastrointestinal dysfunction (diarrhea, inflammatory bowel disease, etc.) shock, bone disease characterized by abnormal bone metabolism such as osteoporosis (especially, postmenopausal osteoporosis), hypercalcemia, hyperparathyroidism, Paget's bone diseases, osteolysis, hypercalcemia of malignancy with or without bone metastases, rheumatoid arthritis, periodontitis, osteoarthritis, ostealgia, osteopenia, cancer cachexia, calculosis, lithiasis (especially, urolithiasis), solid carcinoma, mesangial proliferative glomerulonephritis, edema (e.g. cardiac edema, cerebral edema, etc.), hypertension such as malignant hypertension or the like, premenstrual tension, urinary calculus, oliguria such as the one caused by acute or chronic failure, hyperphosphaturia, or the like."

U.S. Pat. No. 6,710,072 teaches the use of EP2 agonists for the treatment or prevention of "osteoporosis, constipation, renal disorders, sexual dysfunction, baldness, diabetes, cancer and in disorder of immune regulation . . . various pathophysiological diseases including acute myocardial infarction, vascular thrombosis, hypertension, pulmonary hypertension, ischemic heart disease, congestive heart failure, and angina pectoris."

SUMMARY OF THE INVENTION

Disclosed herein are compounds useful in treating glaucoma, inflammatory bowel disease, the stimulation of hair growth, and the stimulation of the conversion of vellus hair to terminal hair. The compounds themselves are disclosed below.

DESCRIPTION OF THE INVENTION

A compound is disclosed herein comprising

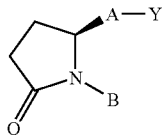

or a pharmaceutically acceptable salt thereof, or a prodrug thereof;
wherein Y is

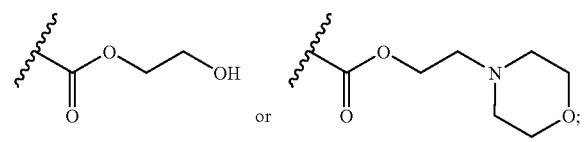

A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be substituted with S or O; or A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O; and
B is aryl or heteroaryl.

In relation to the identity of A disclosed in the chemical structures presented herein, A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be substituted with S or O; or A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O.

While not intending to be limiting, A may be —(CH$_2$)$_6$—, cis-CH$_2$CH=CH—(CH$_2$)$_3$—, or —CH$_2$C≡C—(CH$_2$)$_3$—.

Alternatively, A may be a group which is related to one of these three moieties in that any carbon is substituted with S and/or O. For example, while not intending to limit the scope of the invention in any way, A may be an S substituted moiety such as one of the following or the like.

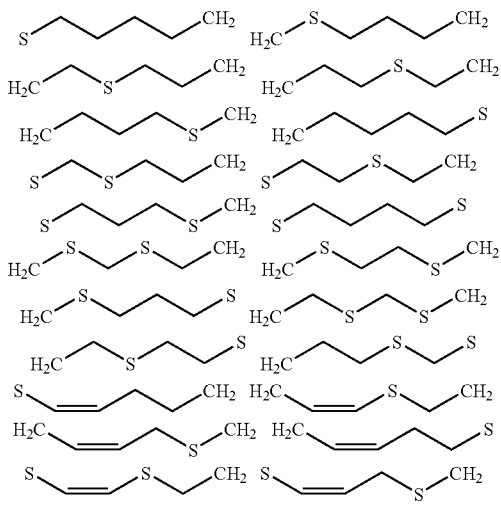

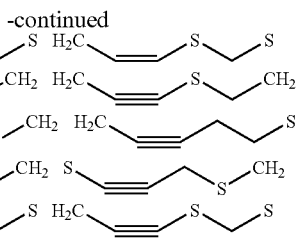

Alternatively, while not intending to limit the scope of the invention in any way, A may be an O substituted moiety such as one of the following or the like.

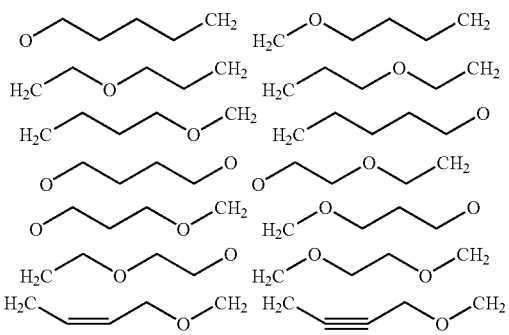

Alternatively, while not intending to limit the scope of the invention in any way, A may have both an O and an S substituted into the chain, such as one of the following or the like.

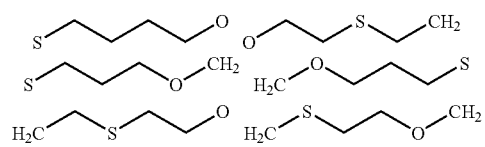

Alternatively, while not intending to limit the scope of the invention in any way, in certain embodiments A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O. In other words, while not intending to limit the scope of the invention in any way, in one embodiment A comprises from 1 to 4 CH$_2$ moieties and Ar, e.g. —CH$_2$—Ar—, —(CH$_2$)$_2$—Ar—, —CH$_2$—Ar—CH$_2$—, —CH$_2$—Ar—(CH$_2$)$_2$—, —(CH$_2$)$_2$—Ar—(CH$_2$)$_2$—, and the like; or A comprises O, from 0 to 3 CH$_2$ moieties, and Ar, e.g., —O—Ar—, Ar—CH$_2$—O—, —O—Ar—(CH$_2$)$_2$—, —O—CH$_2$—Ar—, —O—CH$_2$—Ar—(CH$_2$)$_2$, and the like; or A comprises S, from 0 to 3 CH$_2$ moieties, and Ar, e.g., —S—Ar—, Ar—CH$_2$—S—, —S—Ar—(CH$_2$)$_2$—, —S—CH$_2$—Ar—, —S—CH$_2$—Ar—(CH$_2$)$_2$, —(CH$_2$)$_2$—S—Ar, and the like.

In another embodiment, the sum of m and o is from 2 to 4 wherein one CH$_2$ may be substituted with S or O.

In another embodiment, the sum of m and o is 3 wherein one CH$_2$ may be substituted with S or O.

In another embodiment, the sum of m and o is 2 wherein one CH$_2$ may be substituted with S or O.

In another embodiment, the sum of m and o is 4 wherein one CH$_2$ may be substituted with S or O.

Interarylene or heterointerarylene refers to an aryl ring or ring system or a heteroaryl ring or ring system which connects two other parts of a molecule, i.e. the two parts are bonded to the ring in two distinct ring positions. Interarylene or heterointerarylene may be substituted or unsubstituted. Unsubstituted interarylene or heterointerarylene has no substituents other than the two parts of the molecule it connects. Substituted interarylene or heterointerarylene has one or more substituents in addition to the two parts of the molecule it connects.

In one embodiment, Ar is substituted or unsubstituted interphenylene, interthienylene, interfurylene, interpyridinylene, interoxazolylene, and interthiazolylene. In another embodiment Ar is interphenylene (Ph). In another embodiment A is —(CH$_2$)$_2$-Ph-. While not intending to limit scope of the invention in any way, substituents may have 4 or less heavy atoms, or in other words, non hydrogen atoms. Any number of hydrogen atoms required for a particular substituent will also be included. Thus, the substituent may be hydrocarbyl, i.e. a moiety consisting of only carbon and
  hydrogen such as alkyl, having up to 4 carbon atoms,
    including alkyl up to C$_4$, alkenyl, alkynyl, and the like;
hydrocarbyloxy up to C$_3$;
CF$_3$;
halo, such as F, Cl, or Br;
hydroxyl;
NH$_2$ and alkylamine functional groups up to C$_3$;
other N or S containing substituents;
and the like.

Substituted interarylene or interheteroarylene may have one or more substituents, up to as many as the ring or ring system will bear, and the substituents may be the same or different. Thus, for example, an interarylene ring or interheteroarylene ring may be substituted with chloro and methyl; methyl, OH, and F; CN, NO$_2$, and ethyl; and the like including any conceivable substituent or combination of substituent possible in light of this disclosure.

In one embodiment A is —(CH$_2$)$_m$—Ar—(CH$_2$)$_o$— wherein Ar is interphenylene, the sum of m and o is from 1 to 3, and wherein one CH$_2$ may be substituted with S or O.

In another embodiment A is —CH$_2$—Ar—OCH$_2$—. In another embodiment A is —CH$_2$—Ar—OCH$_2$— and Ar is interphenylene. In another embodiment, Ar is 1,3 interaryl or interheteroaryl, where Ar attached at the 1 and 3 positions, such as when A has the structure shown below.

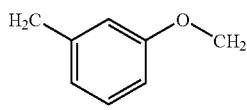

Other examples of 1,3 interaryl or interheteroaryl are exemplified in the following examples of A-Y.

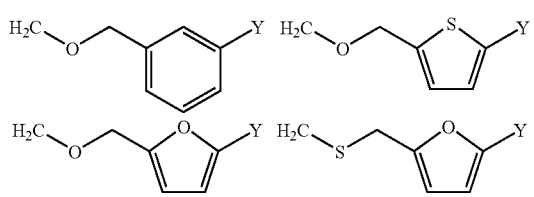

In another embodiment A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be substituted with S or O; or A is —(CH$_2$)$_2$-Ph- wherein one CH$_2$ may be substituted with S or O.

In another embodiment A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be substituted with S or O; or A is —(CH$_2$)$_2$-Ph-.

In another embodiment A is not —(CH$_2$)$_6$—.

In other embodiments, A has one of the following structures, where Y is attached to the oxazolyl or thiazolyl ring.

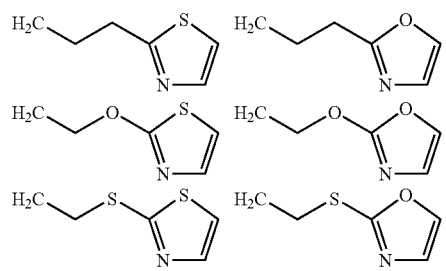

In other embodiments A is one of the structures shown below, where Y is attached to the phenyl or heteroaryl ring.

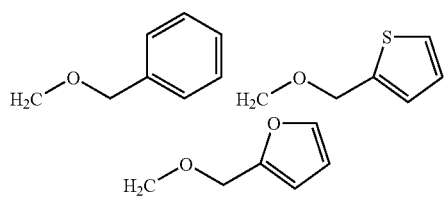

In other embodiments, A has one of the following structures,

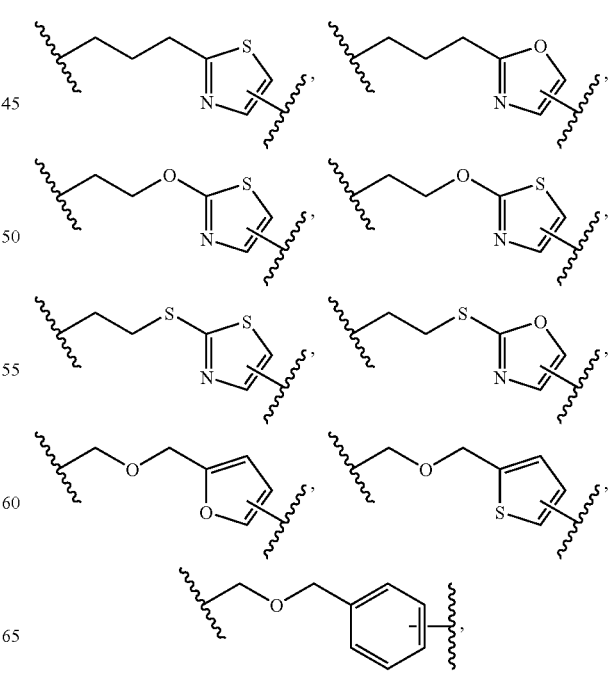

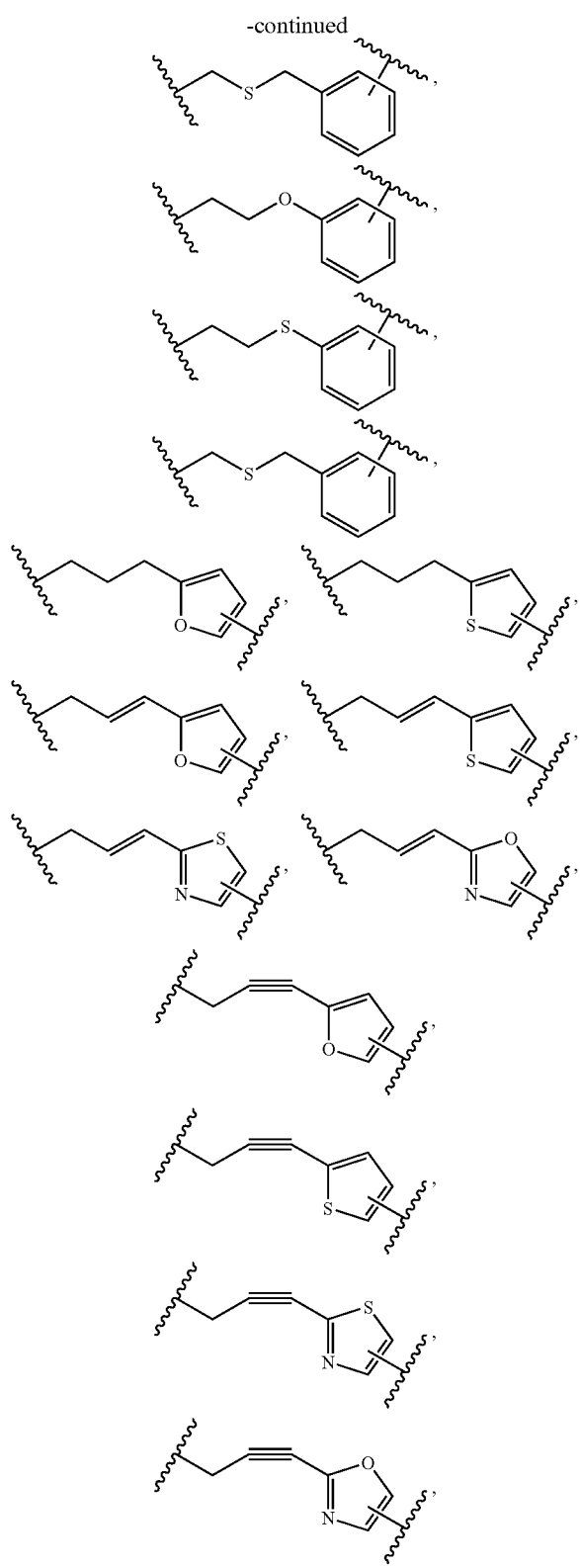

In another embodiment A is —CH$_2$OCH$_2$Ar.
In another embodiment A is —CH$_2$SCH$_2$Ar.
In another embodiment A is —(CH$_2$)$_3$Ar.
In another embodiment A is —CH$_2$O(CH$_2$)$_4$.
In another embodiment A is —CH$_2$S(CH$_2$)$_4$.
In another embodiment A is, —S(CH$_2$)$_3$S(CH$_2$)$_2$—.

In another embodiment A is, —(CH$_2$)$_4$OCH$_2$—.
In another embodiment A is, cis —CH$_2$CH=CH—CH$_2$OCH$_2$—.
In another embodiment A is, —CH$_2$CH≡CH—CH$_2$OCH$_2$—.
In another embodiment A is, —(CH$_2$)$_2$S(CH$_2$)$_3$—.
In another embodiment A is, —CH$_2$-Ph-OCH$_2$—, wherein Ph is interphenylene.
In another embodiment A is, —CH$_2$-mPh-OCH$_2$—, wherein mPh is m-interphenylene.
In another embodiment A is, —CH$_2$—O—(CH$_2$)$_4$—.
In another embodiment A is, —CH$_2$—O—CH$_2$—Ar—, wherein Ar is 2,5-interthienylene.
In another embodiment A is, —CH$_2$—O—CH$_2$—Ar—, wherein Ar is 2,5-interfurylene.

B is aryl or heteroaryl.

Aryl is an unsubstituted or substituted aromatic ring or ring system such as phenyl, naphthyl, biphenyl, and the like.

Heteroaryl is aryl having one or more N, O, or S atoms in the ring, i.e. a ring carbon is substituted by N, O, or S. While not intending to be limiting, examples of heteroaryl include unsubstituted or substituted thienyl, pyridinyl, furyl, benzothienyl, benzofuryl, imidizololyl, indolyl, and the like.

The substituents of aryl or heteroaryl may have up to 12 non-hydrogen atoms each and as many hydrogen atoms as necessary. Thus, while not intending to limit the scope of the invention in any way, the substituents may be:

hydrocarbyl, i.e. a moiety consisting of only carbon and hydrogen such as alkyl, alkenyl, alkynyl, and the like, including linear, branched or cyclic hydrocarbyl, and combinations thereof;

hydrocarbyloxy, meaning O-hydrocarbyl such as OCH$_3$, OCH$_2$CH$_3$, O-cyclohexyl, etc, up to 11 carbon atoms;

other ether substituents such as CH$_2$OCH$_3$, (CH$_2$)$_2$OCH(CH$_3$)$_2$, and the like;

thioether substituents including S-hydrocarbyl and other thioether substituents;

hydroxyhydrocarbyl, meaning hydrocarbyl-OH such as CH$_2$OH, C(CH$_3$)$_2$OH, etc, up to 11 carbon atoms;

nitrogen substituents such as NO$_2$, CN, and the like, including amino, such as NH$_2$, NH(CH$_2$CH$_3$OH), NHCH$_3$, and the like up to 11 carbon atoms;

carbonyl substituents, such as CO$_2$H, ester, amide, and the like;

halogen, such as chloro, fluoro, bromo, and the like fluorocarbyl, such as CF$_3$, CF$_2$CF$_3$, etc.;

phosphorous substituents, such as PO$_3^{2-}$, and the like;

sulfur substituents, including S-hydrocarbyl, SH, SO$_3$H, SO$_2$-hydrocarbyl, SO$_3$-hydrocarbyl, and the like.

In certain embodiments, the number of non-hydrogen atoms is 6 or less in a substituent. In other embodiments, the number of non-hydrogen atoms is 3 or less in a substituent. In other embodiments, the number of non-hydrogen atoms on a substituent is 1.

In certain embodiments, the substituents contain only hydrogen, carbon, oxygen, halogen, nitrogen, and sulfur. In other embodiments, the substituents contain only hydrogen, carbon, oxygen, and halogen.

Unless otherwise indicated, references to aryl, heteroaryl, phenyl, thienyl, benzothienyl, and the like are intended to mean both the substituted and the unsubstituted moiety.

Substituted aryl or heteroaryl may have one or more substituents, up to as many as the ring or ring system will bear, and the substituents may be the same or different. Thus, for example, an aryl ring or a heteroaryl ring may be substituted with chloro and methyl; methyl, OH, and F; CN, NO$_2$, and ethyl; and the like including any conceivable substituent or combination of substituent possible in light of this disclosure.

Thus, compounds wherein B is any of the above classes or species of aryl or heteroaryl are contemplated herein.

Further, while not intending to limit the scope of the invention in any way, in one embodiment B is phenyl. In another embodiment B is chlorophenyl, meaning phenyl with one or more chloro substituents. In another embodiment D is 3,5-dichlorophenyl. In another embodiment B is unsubstituted phenyl. In another embodiment B is alkylphenyl. In another embodiment B is t-butylphenyl.

In another embodiment B is not unsubstituted phenyl. In another embodiment B is not chlorophenyl. In another embodiment B is not fluorophenyl. In another embodiment B is not dimethylaminophenyl. In another embodiment B is not unsubstituted phenyl, chlorophenyl, fluorophenyl, or dimethylaminophenyl.

In another embodiment B is hydroxyalkylphenyl, meaning phenyl with a hydroxyalkyl substitutent such as Ph-CH(OH)C(CH$_3$)$_3$.

B can also be any of the groups shown below, where the remainder of the molecule attaches to the phenyl ring. The names of these moieties are shown to the right of the structure.

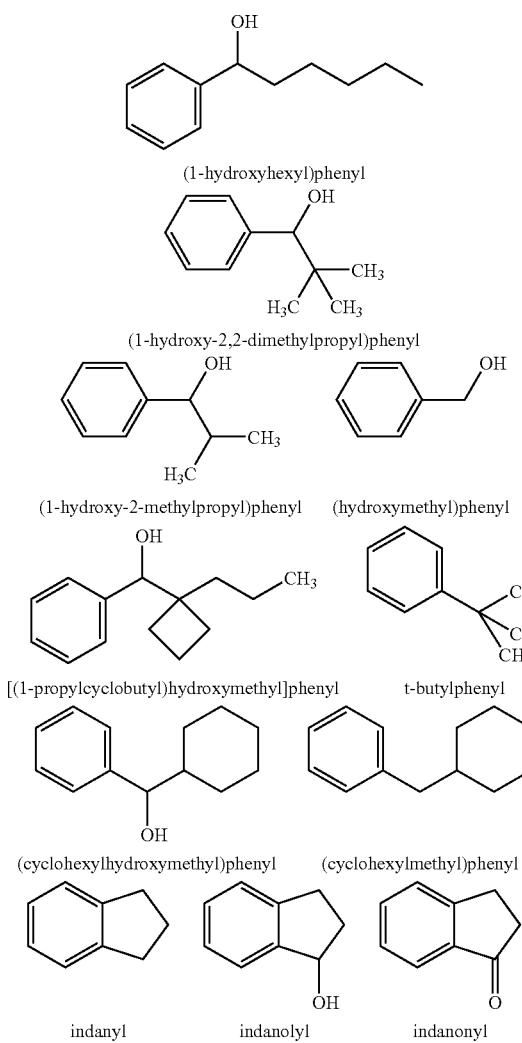

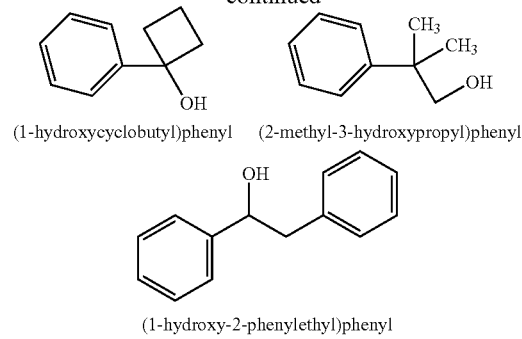

One compound comprises

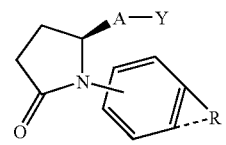

or a pharmaceutically acceptable salt thereof, or a prodrug thereof;
wherein a dashed line indicates the presence or absence of a bond
R is hydrocarbyl or hydroxyhydrocarbyl having from 1 to 12 carbon atoms.

Another embodiment comprises

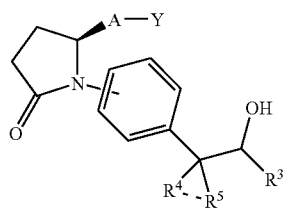

or a pharmaceutically acceptable salt thereof, or a prodrug thereof;
wherein a dashed line indicates the presence or absence of a bond;
R$^3$, R$^4$, and R$^5$ are independently H or C$_{1-6}$ alkyl.

As the dashed line indicates the presence or absence of a bond, R$^4$ and R$^5$ may be two separate moieties. For example, while not intending to be limiting, in one embodiment R$^4$ and R$^5$ is methyl, and no bond is present where indicated by the dashed line.

For example, a compound according to the formula below

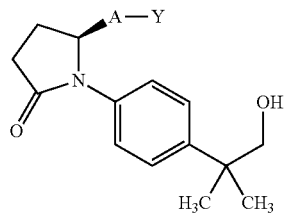

or a pharmaceutically acceptable salt thereof, or a prodrug thereof is contemplated. Alternatively, while not intending to limit the scope of the invention in any way, $R^4$ and $R^5$ may form a ring. In other words, a compound such as the one shown below is possible, wherein x is from 1 to 6.

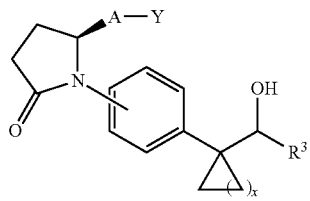

A pharmaceutically acceptable salt thereof, or a prodrug thereof is also contemplated.

Another embodiment comprises

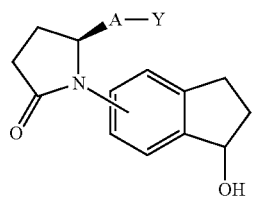

A pharmaceutically acceptable salt thereof, or a prodrug thereof is also contemplated.

Other useful compounds comprise

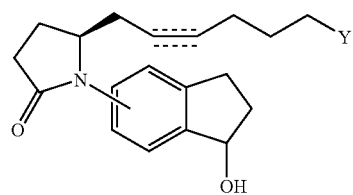

A pharmaceutically acceptable salt thereof, or a prodrug thereof is also contemplated.

Other useful examples of compounds comprise

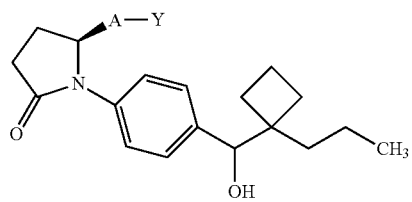

or a pharmaceutically acceptable salt thereof, or a prodrug thereof.

Other compounds comprise

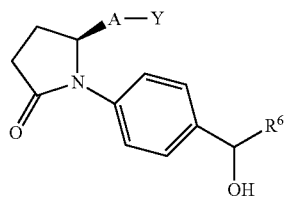

or a pharmaceutically acceptable salt thereof, or a prodrug thereof, wherein $R^6$ is cycloalkyl comprising from 3 to 10 carbon atoms.

Other compounds comprise

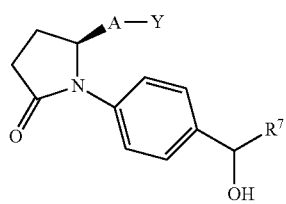

or a pharmaceutically acceptable salt thereof, or a prodrug thereof, wherein $R^7$ is linear alkyl comprising from 3 to 7 carbon atoms.

Other compounds comprise

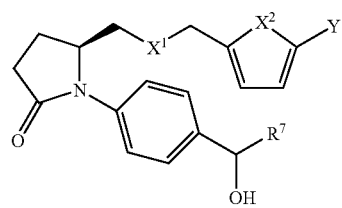

or a pharmaceutically acceptable salt thereof, or a prodrug thereof, wherein $X^1$ and $X^2$ are independently CH, O, or S; and $R^7$ is linear alkyl comprising from 3 to 7 carbon atoms.

Other compounds comprise

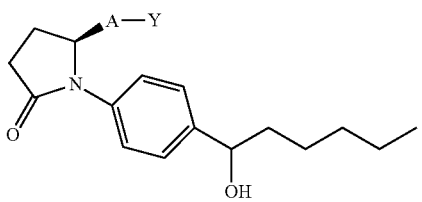

or a pharmaceutically acceptable salt thereof, or a prodrug thereof.

Other compounds comprise

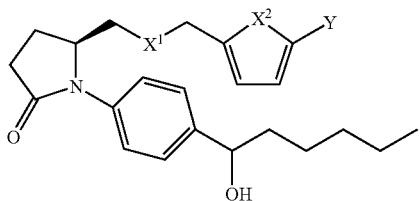

or a pharmaceutically acceptable salt thereof, or a prodrug thereof,
wherein $X^1$ and $X^2$ are independently CH, O, or S.

Other compounds comprise

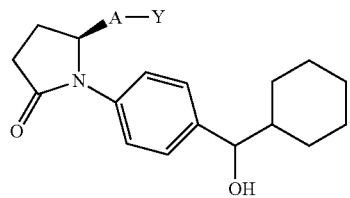

or a pharmaceutically acceptable salt thereof, or a prodrug thereof.

Other compounds comprise

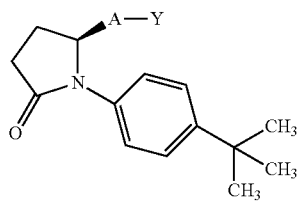

or a pharmaceutically acceptable salt thereof, or a prodrug thereof.

Another useful compound is

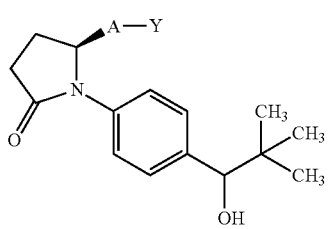

or a pharmaceutically acceptable salt thereof, or a prodrug thereof.

Another useful compound is

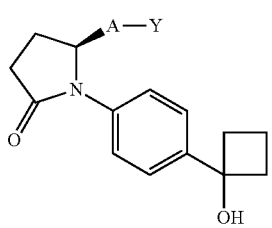

or a pharmaceutically acceptable salt thereof, or a prodrug thereof.

Another compound comprises

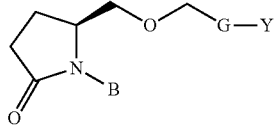

or a pharmaceutically acceptable salt thereof, or a prodrug thereof;
wherein G is 1,3-interaryl or interheteroaryl, or —(CH$_2$)$_3$—.

Another compound comprises

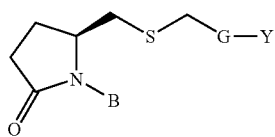

or a pharmaceutically acceptable salt thereof, or a prodrug thereof;
wherein G is 1,3-interaryl or interheteroaryl, or —(CH$_2$)$_3$—.

Another compound comprises

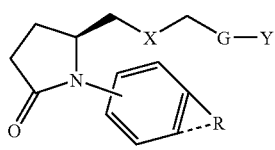

or a pharmaceutically acceptable salt thereof, or a prodrug thereof;
wherein a dashed line indicates the presence or absence of a bond;
R is hydrocarbyl or hydroxyhydrocarbyl having from 1 to 12 carbon atoms;
X is CH$_2$, O, or S; and
G is 1,3-interaryl or interheteroaryl, or —(CH$_2$)$_3$—.

Another compound is an N-aryl or N-heteroaryl gamma lactam which is active at a prostaglandin receptor. This compound may or may not incorporate any other structural limitation disclosed herein.

Another compound is an N-aryl or N-heteroaryl gamma lactam which is selectively active at a prostaglandin EP$_2$ receptor. This compound may or may not incorporate any other structural limitation disclosed herein.

Another compound is an N-aryl or N-heteroaryl gamma lactam which is effective at reducing intraocular pressure in a mammal. This compound may or may not incorporate any other structural limitation disclosed herein.

The determination of whether a compound is active at a prostaglandin receptor is well within the ability of a person of ordinary skill in the art. The determination of whether a compound is active at a prostaglandin EP$_2$ receptor is also well within the ability of a person of ordinary skill in the art. While not intending to limit the scope of the invention in any way, one method of making such determinations is also provided in the examples herein.

The determination of whether a compound is effective at reducing intraocular pressure in a mammal is well within the ability of a person of ordinary skill in the art. While not intending to limit the scope of the invention in any way, methods of determining whether a compound is effective in reducing intraocular pressure are given for a few exemplary mammals herein.

While not intending to limit the scope of the invention in any way, examples of useful compounds are depicted below, and pharmaceutically acceptable salts or prodrugs thereof.

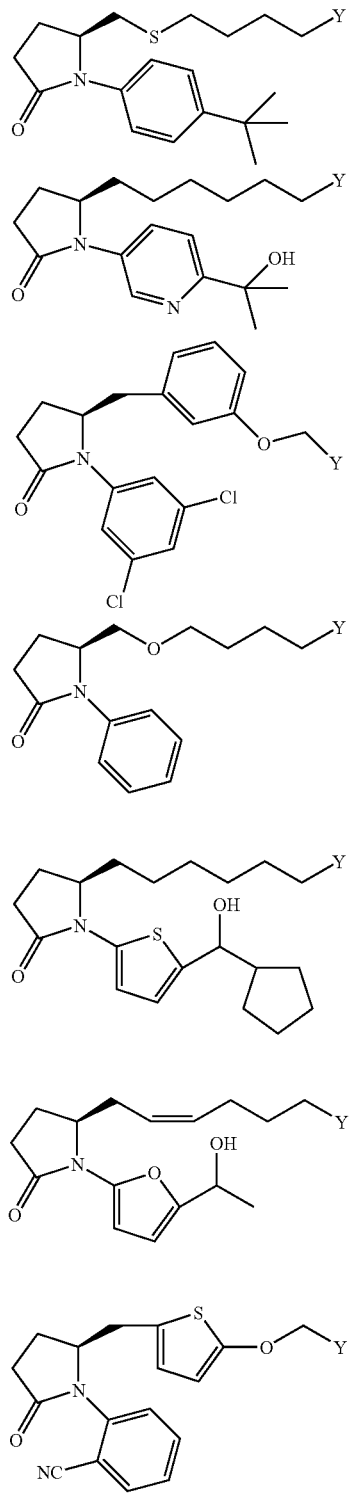

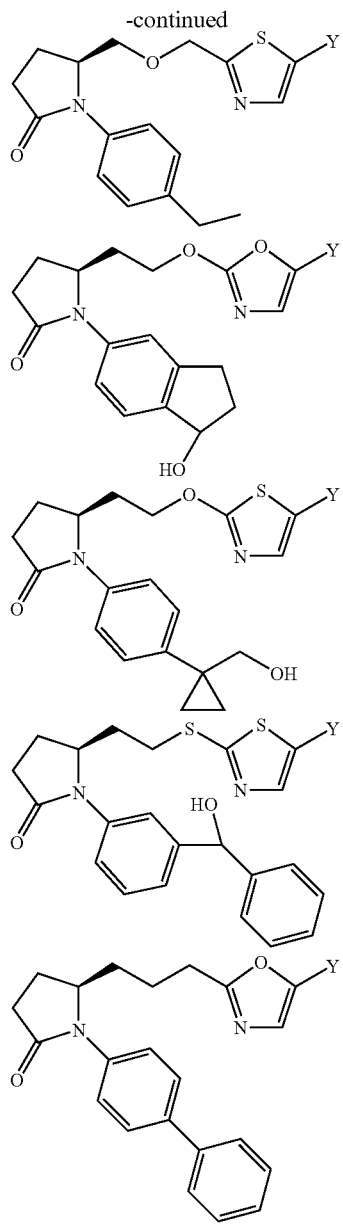

In one embodiment A is —S(CH$_2$)$_3$S(CH$_2$)$_2$— and B is phenyl.

In another embodiment A is —(CH$_2$)$_4$OCH$_2$— and B is phenyl.

In another embodiment A is cis —CH$_2$CH=CH— CH$_2$OCH$_2$— and B is phenyl.

In another embodiment A is —CH$_2$CH≡CH— CH$_2$OCH$_2$— and B is phenyl.

In another embodiment A is —(CH$_2$)$_2$S(CH$_2$)$_3$— and B is phenyl.

In another embodiment A is —CH$_2$-Ph-OCH$_2$—, wherein Ph is interphenylene, and B is phenyl.

In another embodiment A is —CH$_2$-mPh-OCH$_2$—, wherein mPh is m-interphenylene, and B is phenyl.

In another embodiment A is —CH$_2$—O—(CH$_2$)$_4$— and B is phenyl.

In another embodiment A is —CH$_2$—O—CH$_2$—Ar—, wherein Ar is 2,5-interthienylene, and B is phenyl.

In another embodiment A is —CH$_2$—O—CH$_2$—Ar—, wherein Ar is 2,5-interfurylene, and B is phenyl.

As mentioned before, phenyl in the above embodiments means substituted or unsubstituted phenyl unless indicated otherwise.

In one embodiment A is —S(CH$_2$)$_3$S(CH$_2$)$_2$— and B is (1-hydroxyhexyl)phenyl.

In another embodiment A is —(CH$_2$)$_4$OCH$_2$— and B is (1-hydroxyhexyl)phenyl.

In another embodiment A is cis —CH$_2$CH═CH—CH$_2$OCH$_2$— and B is (1-hydroxyhexyl)phenyl.

In another embodiment A is —CH$_2$CH≡CH—CH$_2$OCH$_2$— and B is (1-hydroxyhexyl)phenyl.

In another embodiment A is —(CH$_2$)$_2$S(CH$_2$)$_3$— and B is (1-hydroxyhexyl)phenyl.

In another embodiment A is —CH$_2$-Ph-OCH$_2$—, wherein Ph is interphenylene, and B is (1-hydroxyhexyl)phenyl.

In another embodiment A is —CH$_2$-mPh-OCH$_2$—, wherein mPh is m-interphenylene, and B is (1-hydroxyhexyl)phenyl.

In another embodiment A is —CH$_2$—O—(CH$_2$)$_4$— and B is (1-hydroxyhexyl)phenyl.

In another embodiment A is —CH$_2$—O—CH$_2$—Ar—, wherein Ar is 2,5-interthienylene, and B is (1-hydroxyhexyl)phenyl.

In another embodiment A is —CH$_2$—O—CH$_2$—Ar—, wherein Ar is 2,5-interfurylene, and B is (1-hydroxyhexyl)phenyl.

In another embodiment A is —S(CH$_2$)$_3$S(CH$_2$)$_2$— and B is (1-hydroxy-2,2-dimethylpropyl)phenyl.

In another embodiment A is —(CH$_2$)$_4$OCH$_2$— and B is (1-hydroxy-2,2-dimethylpropyl)phenyl.

In another embodiment A is cis —CH$_2$CH═CH—CH$_2$OCH$_2$— and B is (1-hydroxy-2,2-dimethylpropyl)phenyl.

In another embodiment A is —CH$_2$CH≡CH—CH$_2$OCH$_2$— and B is (1-hydroxy-2,2-dimethylpropyl)phenyl.

In another embodiment A is —(CH$_2$)$_2$S(CH$_2$)$_3$— and B is (1-hydroxy-2,2-dimethylpropyl)phenyl.

In another embodiment A is —CH$_2$-Ph-OCH$_2$—, wherein Ph is interphenylene, and B is (1-hydroxy-2,2-dimethylpropyl)phenyl.

In another embodiment A is —CH$_2$-mPh-OCH$_2$—, wherein mPh is m-interphenylene, and B is (1-hydroxy-2,2-dimethylpropyl)phenyl.

In another embodiment A is —CH$_2$—O—(CH$_2$)$_4$— and B is (1-hydroxy-2,2-dimethylpropyl)phenyl.

In another embodiment A is —CH$_2$—O—CH$_2$—Ar—, wherein Ar is 2,5-interthienylene, and B is (1-hydroxy-2,2-dimethylpropyl)phenyl.

In another embodiment A is —CH$_2$—O—CH$_2$—Ar—, wherein Ar is 2,5-interfurylene, and B is (1-hydroxy-2,2-dimethylpropyl)phenyl.

In another embodiment A is —S(CH$_2$)$_3$S(CH$_2$)$_2$— and B is (1-hydroxy-2-methylpropyl)phenyl.

In another embodiment A is —(CH$_2$)$_4$OCH$_2$— and B is (1-hydroxy-2-methylpropyl)phenyl.

In another embodiment A is cis —CH$_2$CH═CH—CH$_2$OCH$_2$— and B is (1-hydroxy-2-methylpropyl)phenyl.

In another embodiment A is —CH$_2$CH≡CH—CH$_2$OCH$_2$— and B is (1-hydroxy-2-methylpropyl)phenyl.

In another embodiment A is —(CH$_2$)$_2$S(CH$_2$)$_3$— and B is (1-hydroxy-2-methylpropyl)phenyl.

In another embodiment A is —CH$_2$-Ph-OCH$_2$—, wherein Ph is interphenylene, and B is (1-hydroxy-2-methylpropyl)phenyl.

In another embodiment A is —CH$_2$-mPh-OCH$_2$—, wherein mPh is m-interphenylene, and B is (1-hydroxy-2-methylpropyl)phenyl.

In another embodiment A is —CH$_2$—O—(CH$_2$)$_4$— and B is (1-hydroxy-2-methylpropyl)phenyl.

In another embodiment A is —CH$_2$—O—CH$_2$—Ar—, wherein Ar is 2,5-interthienylene, and B is (1-hydroxy-2-methylpropyl)phenyl.

In another embodiment A is —CH$_2$—O—CH$_2$—Ar—, wherein Ar is 2,5-interfurylene, and B is (1-hydroxy-2-methylpropyl)phenyl.

In another embodiment A is —S(CH$_2$)$_3$S(CH$_2$)$_2$— and B is (hydroxymethyl)phenyl.

In another embodiment A is —(CH$_2$)$_4$OCH$_2$— and B is (hydroxymethyl)phenyl.

In another embodiment A is cis —CH$_2$CH═CH—CH$_2$OCH$_2$— and B is (hydroxymethyl)phenyl.

In another embodiment A is —CH$_2$CH≡CH—CH$_2$OCH$_2$— and B is (hydroxymethyl)phenyl.

In another embodiment A is —(CH$_2$)$_2$S(CH$_2$)$_3$— and B is (hydroxymethyl)phenyl.

In another embodiment A is —CH$_2$-Ph-OCH$_2$—, wherein Ph is interphenylene, and B is (hydroxymethyl)phenyl.

In another embodiment A is —CH$_2$-mPh-OCH$_2$—, wherein mPh is m-interphenylene, and B is (hydroxymethyl)phenyl.

In another embodiment A is —CH$_2$—O—(CH$_2$)$_4$— and B is (hydroxymethyl)phenyl.

In another embodiment A is —CH$_2$—O—CH$_2$—Ar—, wherein Ar is 2,5-interthienylene, and B is (hydroxymethyl)phenyl.

In another embodiment A is —CH$_2$—O—CH$_2$—Ar—, wherein Ar is 2,5-interfurylene, and B is (hydroxymethyl)phenyl.

In another embodiment A is —S(CH$_2$)$_3$S(CH$_2$)$_2$— and B is [(1-propylcyclobutyl)hydroxymethyl]phenyl.

In another embodiment A is —(CH$_2$)$_4$OCH$_2$— and B is [(1-propylcyclobutyl)hydroxymethyl]phenyl.

In another embodiment A is cis —CH$_2$CH═CH—CH$_2$OCH$_2$— and B is [(1-propylcyclobutyl)hydroxymethyl]phenyl.

In another embodiment A is —CH$_2$CH≡CH—CH$_2$OCH$_2$— and B is [(1-propylcyclobutyl)hydroxymethyl]phenyl.

In another embodiment A is —(CH$_2$)$_2$S(CH$_2$)$_3$— and B is [(1-propylcyclobutyl)hydroxymethyl]phenyl.

In another embodiment A is —CH$_2$-Ph-OCH$_2$—, wherein Ph is interphenylene, and B is [(1-propylcyclobutyl)hydroxymethyl]phenyl.

In another embodiment A is —CH$_2$-mPh-OCH$_2$—, wherein mPh is m-interphenylene, and B is [(1-propylcyclobutyl)hydroxymethyl]phenyl.

In another embodiment A is —CH$_2$—O—(CH$_2$)$_4$— and B is [(1-propylcyclobutyl)hydroxymethyl]phenyl.

In another embodiment A is —CH$_2$—O—CH$_2$—Ar—, wherein Ar is 2,5-interthienylene, and B is [(1-propylcyclobutyl)hydroxymethyl]phenyl.

In another embodiment A is —CH$_2$—O—CH$_2$—Ar—, wherein Ar is 2,5-interfurylene, and B is [(1-propylcyclobutyl)hydroxymethyl]phenyl.

In another embodiment A is —S(CH$_2$)$_3$S(CH$_2$)$_2$— and B is t-butylphenyl.

In another embodiment A is —(CH$_2$)$_4$OCH$_2$— and B is t-butylphenyl.

In another embodiment A is cis —CH$_2$CH═CH—CH$_2$OCH$_2$— and B is t-butylphenyl.

In another embodiment A is —CH₂CH≡CH—CH₂OCH₂— and B is t-butylphenyl.

In another embodiment A is —(CH₂)₂S(CH₂)₃— and B is t-butylphenyl.

In another embodiment A is —CH₂-Ph-OCH₂—, wherein Ph is interphenylene, and B is t-butylphenyl.

In another embodiment A is —CH₂-mPh-OCH₂—, wherein mPh is m-interphenylene, and B is t-butylphenyl.

In another embodiment A is —CH₂—O—(CH₂)₄— and B is t-butylphenyl.

In another embodiment A is —CH₂—O—CH₂—Ar—, wherein Ar is 2,5-interthienylene, and B is t-butylphenyl.

In another embodiment A is —CH₂—O—CH₂—Ar—, wherein Ar is 2,5-interfurylene, and B is t-butylphenyl.

In another embodiment A is —S(CH₂)₃S(CH₂)₂— and B is (cyclohexylhydroxymethyl)phenyl.

In another embodiment A is —(CH₂)₄OCH₂— and B is (cyclohexylhydroxymethyl)phenyl.

In another embodiment A is cis —CH₂CH═CH—CH₂OCH₂— and B is (cyclohexylhydroxymethyl)phenyl.

In another embodiment A is —CH₂CH≡CH—CH₂OCH₂— and B is (cyclohexylhydroxymethyl)phenyl.

In another embodiment A is —(CH₂)₂S(CH₂)₃— and B is (cyclohexylhydroxymethyl)phenyl.

In another embodiment A is —CH₂-Ph-OCH₂—, wherein Ph is interphenylene, and B is (cyclohexylhydroxymethyl)phenyl.

In another embodiment A is —CH₂-mPh-OCH₂—, wherein mPh is m-interphenylene, and B is (cyclohexylhydroxymethyl)phenyl.

In another embodiment A is —CH₂—O—(CH₂)₄— and B is (cyclohexylhydroxymethyl)phenyl.

In another embodiment A is —CH₂—O—CH₂—Ar—, wherein Ar is 2,5-interthienylene, and B is (cyclohexylhydroxymethyl)phenyl.

In another embodiment A is —CH₂—O—CH₂—Ar—, wherein Ar is 2,5-interfurylene, and B is (cyclohexylhydroxymethyl)phenyl.

In another embodiment A is —S(CH₂)₃S(CH₂)₂— and B is (cyclohexylmethyl)phenyl.

In another embodiment A is —(CH₂)₄OCH₂— and B is (cyclohexylmethyl)phenyl.

In another embodiment A is cis —CH₂CH═CH—CH₂OCH₂— and B is (cyclohexylmethyl)phenyl.

In another embodiment A is —CH₂CH≡CH—CH₂OCH₂— and B is (cyclohexylmethyl)phenyl.

In another embodiment A is —(CH₂)₂S(CH₂)₃— and B is (cyclohexylmethyl)phenyl.

In another embodiment A is —CH₂-Ph-OCH₂—, wherein Ph is interphenylene, and B is (cyclohexylmethyl)phenyl.

In another embodiment A is —CH₂-mPh-OCH₂—, wherein mPh is m-interphenylene, and B is (cyclohexylmethyl)phenyl.

In another embodiment A is —CH₂—O—(CH₂)₄— and B is (cyclohexylmethyl)phenyl.

In another embodiment A is —CH₂—O—CH₂—Ar—, wherein Ar is 2,5-interthienylene, and B is (cyclohexylmethyl)phenyl.

In another embodiment A is —CH₂—O—CH₂—Ar—, wherein Ar is 2,5-interfurylene, and B is (cyclohexylmethyl)phenyl.

In another embodiment A is —S(CH₂)₃S(CH₂)₂— and B is indanyl.

In another embodiment A is —(CH₂)₄OCH₂— and B is indanyl.

In another embodiment A is cis —CH₂CH═CH—CH₂OCH₂— and B is indanyl.

In another embodiment A is —CH₂CH≡CH—CH₂OCH₂— and B is indanyl.

In another embodiment A is —(CH₂)₂S(CH₂)₃— and B is indanyl.

In another embodiment A is —CH₂-Ph-OCH₂—, wherein Ph is interphenylene, and B is indanyl.

In another embodiment A is —CH₂-mPh-OCH₂—, wherein mPh is m-interphenylene, and B is indanyl.

In another embodiment A is —CH₂—O—(CH₂)₄— and B is indanyl.

In another embodiment A is —CH₂—O—CH₂—Ar—, wherein Ar is 2,5-interthienylene, and B is indanyl.

In another embodiment A is —CH₂—O—CH₂—Ar—, wherein Ar is 2,5-interfurylene, and B is indanyl.

In another embodiment A is —S(CH₂)₃S(CH₂)₂— and B is indanolyl.

In another embodiment A is —(CH₂)₄OCH₂— and B is indanolyl.

In another embodiment A is cis —CH₂CH═CH—CH₂OCH₂— and B is indanolyl.

In another embodiment A is —CH₂CH≡CH—CH₂OCH₂— and B is indanolyl.

In another embodiment A is —(CH₂)₂S(CH₂)₃— and B is indanolyl.

In another embodiment A is —CH₂-Ph-OCH₂—, wherein Ph is interphenylene, and B is indanolyl.

In another embodiment A is —CH₂-mPh-OCH₂—, wherein mPh is m-interphenylene, and B is indanolyl.

In another embodiment A is —CH₂—O—(CH₂)₄— and B is indanolyl.

In another embodiment A is —CH₂—O—CH₂—Ar—, wherein Ar is 2,5-interthienylene, and B is indanolyl.

In another embodiment A is —CH₂—O—CH₂—Ar—, wherein Ar is 2,5-interfurylene, and B is indanolyl.

In another embodiment A is —S(CH₂)₃S(CH₂)₂— and B is indanonyl.

In another embodiment A is —(CH₂)₄OCH₂— and B is indanonyl.

In another embodiment A is cis —CH₂CH═CH—CH₂OCH₂— and B is indanonyl.

In another embodiment A is —CH₂CH≡CH—CH₂OCH₂— and B is indanonyl.

In another embodiment A is —(CH₂)₂S(CH₂)₃— and B is indanonyl.

In another embodiment A is —CH₂-Ph-OCH₂—, wherein Ph is interphenylene, and B is indanonyl.

In another embodiment A is —CH₂-mPh-OCH₂—, wherein mPh is m-interphenylene, and B is indanonyl.

In another embodiment A is —CH₂—O—(CH₂)₄— and B is indanonyl.

In another embodiment A is —CH₂—O—CH₂—Ar—, wherein Ar is 2,5-interthienylene, and B is indanonyl.

In another embodiment A is —CH₂—O—CH₂—Ar—, wherein Ar is 2,5-interfurylene, and B is indanonyl.

In another embodiment A is —S(CH₂)₃S(CH₂)₂— and B is (1-hydroxycyclobutyl)phenyl.

In another embodiment A is —(CH₂)₄OCH₂— and B is (1-hydroxycyclobutyl)phenyl.

In another embodiment A is cis —CH₂CH═CH—CH₂OCH₂— and B is (1-hydroxycyclobutyl)phenyl.

In another embodiment A is —CH₂CH≡CH—CH₂OCH₂— and B is (1-hydroxycyclobutyl)phenyl.

In another embodiment A is —(CH₂)₂S(CH₂)₃— and B is (1-hydroxycyclobutyl)phenyl.

In another embodiment A is —CH₂-Ph-OCH₂—, wherein Ph is interphenylene, and B is (1-hydroxycyclobutyl)phenyl.

In another embodiment A is —CH$_2$-mPh-OCH$_2$—, wherein mPh is m-interphenylene, and B is (1-hydroxycyclobutyl)phenyl.

In another embodiment A is —CH$_2$—O—(CH$_2$)$_4$— and B is (1-hydroxycyclobutyl)phenyl.

In another embodiment A is —CH$_2$—O—CH$_2$—Ar—, wherein Ar is 2,5-interthienylene, and B is (1-hydroxycyclobutyl)phenyl.

In another embodiment A is —CH$_2$—O—CH$_2$—Ar—, wherein Ar is 2,5-interfurylene, and B is (1-hydroxycyclobutyl)phenyl.

In another embodiment A is —S(CH$_2$)$_3$S(CH$_2$)$_2$— and B is (2-methyl-3-hydroxypropyl)phenyl.

In another embodiment A is —(CH$_2$)$_4$OCH$_2$— and B is (2-methyl-3-hydroxypropyl)phenyl.

In another embodiment A is cis —CH$_2$CH=CH—CH$_2$OCH$_2$— and B is (2-methyl-3-hydroxypropyl)phenyl.

In another embodiment A is —CH$_2$CH≡CH—CH$_2$OCH$_2$— and B is (2-methyl-3-hydroxypropyl)phenyl.

In another embodiment A is —(CH$_2$)$_2$S(CH$_2$)$_3$— and B is (2-methyl-3-hydroxypropyl)phenyl.

In another embodiment A is —CH$_2$-Ph-OCH$_2$—, wherein Ph is interphenylene, and B is (2-methyl-3-hydroxypropyl)phenyl.

In another embodiment A is —CH$_2$-mPh-OCH$_2$—, wherein mPh is m-interphenylene, and B is (2-methyl-3-hydroxypropyl)phenyl.

In another embodiment A is —CH$_2$—O—(CH$_2$)$_4$— and B is (2-methyl-3-hydroxypropyl)phenyl.

In another embodiment A is —CH$_2$—O—CH$_2$—Ar—, wherein Ar is 2,5-interthienylene, and B is (2-methyl-3-hydroxypropyl)phenyl.

In another embodiment A is —CH$_2$—O—CH$_2$—Ar—, wherein Ar is 2,5-interfurylene, and B is (2-methyl-3-hydroxypropyl)phenyl.

In another embodiment A is —S(CH$_2$)$_3$S(CH$_2$)$_2$— and B is (1-hydroxy-2-phenylethyl)phenyl.

In another embodiment A is —(CH$_2$)$_4$OCH$_2$— and B is (1-hydroxy-2-phenylethyl)phenyl.

In another embodiment A is cis —CH$_2$CH=CH—CH$_2$OCH$_2$— and B is (1-hydroxy-2-phenylethyl)phenyl.

In another embodiment A is —CH$_2$CH≡CH—CH$_2$OCH$_2$— and B is (1-hydroxy-2-phenylethyl)phenyl.

In another embodiment A is —(CH$_2$)$_2$S(CH$_2$)$_3$— and B is (1-hydroxy-2-phenylethyl)phenyl.

In another embodiment A is —CH$_2$-Ph-OCH$_2$—, wherein Ph is interphenylene, and B is (1-hydroxy-2-phenylethyl)phenyl.

In another embodiment A is —CH$_2$-mPh-OCH$_2$—, wherein mPh is m-interphenylene, and B is (1-hydroxy-2-phenylethyl)phenyl.

In another embodiment A is —CH$_2$—O—(CH$_2$)$_4$— and B is (1-hydroxy-2-phenylethyl)phenyl.

In another embodiment A is —CH$_2$—O—CH$_2$—Ar—, wherein Ar is 2,5-interthienylene, and B is (1-hydroxy-2-phenylethyl)phenyl.

In another embodiment A is —CH$_2$—O—CH$_2$—Ar—, wherein Ar is 2,5-interfurylene, and B is (1-hydroxy-2-phenylethyl)phenyl.

The compounds of disclosed herein are useful for the prevention or treatment of glaucoma or ocular hypertension in mammals, or for the manufacture of a medicament for the treatment of glaucoma or ocular hypertension. They are also useful for the treatment of those diseases disclosed in the art as being amenable to treatment by prostaglandin EP$_2$ agonist, such as the ones listed previously.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. An ester may be derived from a carboxylic acid of C$_1$ (i.e. the terminal carboxylic acid of a natural prostaglandin), or an ester may be derived from a carboxylic acid functional group on another part of the molecule, such as on a phenyl ring. While not intending to be limiting, an ester may be an alkyl ester, an aryl ester, or a heteroaryl ester. The term alkyl has the meaning generally understood by those skilled in the art and refers to linear, branched, or cyclic alkyl moieties. C$_{1-6}$ alkyl esters are particularly useful, where alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1-6 carbon atoms, etc.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distcarate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds is preferably in the range of about 0.5 or about 1 to about 100 mg/kg/day.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 0-10 |
| buffer | 0.01-10 |
| pH adjustor | q.s. pH 4.5-7.5 |
| antioxidant | as needed |
| surfactant | as needed |
| purified water | as needed to make 100% |

Applications for Stimulating Hair Growth

In one embodiment, the compounds disclosed herein can be useful in the treatment of baldness and/or hair loss. Alopecia (baldness) is a deficiency of either normal or abnormal hair, and is primarily a cosmetic problem in humans. It is a deficiency of terminal hair, the broad diameter, colored hair that is readily seen. However, in the so called bald person, although there is a noticeable absence of terminal hair, the skin does contain vellus hair, which is a fine colorless hair which may require microscopic examination to determine its presence. This vellus hair is a precursor to terminal hair.

The compounds described herein can be used to stimulate, such as the conversion of vellus hair to growth as terminal hair, as well as increasing the rate of growth of terminal hair. The utility of the compounds described herein for the simulation of hair growth was discovered as follows.

In the course of treating patients having glaucoma, treatment may only be appropriate in one eye. Within the course of daily practice, it was discovered that a patient who had been treated with bimatoprost, a prostaglandin analogue, developed lashed that were longer, thicker, and fuller in the treated eye than in the non-treated eye. On examination, the difference was found to be very striking. The lashes were longer and had a fuller, denser appearance in the treated eye. The lash appearance on the lids of the treated eyes would have appeared quite attractive if it represented a bilateral phenomenon. As a result of its asymmetric nature, the long lashes on one side could be construed as disturbing from a cosmetic standpoint. A systemic examination was preformed as a result of the asymmetric phenomenon. It soon became apparent that this altered appearance was not an isolated finding. Comparison of the lids of patients who were taking bimatoprost in only one eye revealed subtle changes in the lashed and adjacent hairs of the bimatoprost-treated side in several patients. Definite differences could be identified to varying degrees in the lashes and adjacent hairs of all patients who were taking the drug on a unilateral basis for longer than 6 months.

The changes in the lashes were apparent on gross inspection in several patients once attention was focused on the issue. In those with light colored hair and lashes, the differences were only seen easily with the aid of the high magnification and lighting capabilities of the slit lamp biomicroscope. In the course of glaucoma follow-up examination, attention is generally immediately focused on the eye itself. As a result of the high power magnification needed only one eye is seen at a time and the eye is seen at a high enough power that the lashes are not in focus. At these higher powers, any lash asymmetry between the two eyes is not likely to be noticed except by careful systematic comparison of the lashes and adjacent hairs of the eyelids of the two eyes.

Observed parameters leading to the conclusion that more robust hair growth occurred in the treatment area following administration of the prostaglandin analogue were multiple. They included increased length of lashed, increased number of lashes along the normal lash line, increased thickness and luster of lashes, increased auxiliary lash-like terminal hair in transitional areas adjacent to areas of normal lash growth, increased auxiliary lash-like terminal hairs at the medial and lateral canthal area, increased pigmentation of the lashes, increased numbers, increased length, as well as increased luster, and thickness of fine hair on the skin of the adjacent lid, and finally, increased perpendicular angulation of lashes and lash-like terminal hairs. The conclusion that hair growth is stimulated by prostaglandin analogues such as bimatoprost is thus supported not by evidence of a difference in a single parameter, but is based on multiple parameters of hair appearance in treated versus control areas in many subjects.

The compounds described herein are prostaglandin analogues and therefore have similar activities as bimatoprost, contain structural similarities, and therefore are expected to stimulate hair growth and stimulation of the conversion of vellus hair to terminal hair. In one embodiment, the compounds described herein and their prodrugs can be used for the stimulation of hair growth. As used herein, hair growth includes hair associated with the scalp, eyebrows, eyelids, beard, and other areas of the skin of animals.

In one embodiment, the compound is mixed with a dermatologically compatible vehicle or carrier. The vehicle, which may be employed for preparing compositions as described herein, may comprise, for example, aqueous solutions such as e.g., physiological salines, oil solutions, or ointments. The vehicle furthermore may contain dermatologically compatible preservatives such as e.g., benzalkonium chloride, surfactants like e.g., polysorbate 80, liposomes or polymers, for example, methyl cellulose, polyvinyl alcohol, polyvinyl pyrrolidone and hyaluronic acid; these may be used for increasing the viscosity. Furthermore, it is also possible to use soluble or insoluble drug inserts when the drug is to be administered.

In one embodiment, dermatological compositions can be formulated for topical treatment for the stimulation of hair growth which comprises an effective hair growth simulating amount of one or more compounds as defined above and a dermatologically compatible carrier. Effective amounts of the active compounds may be determined by one of ordinary skill in the art, but will vary depending on the compound employed, frequency of application and desired result. The compound will generally range from about 0.0000001 to about 50% by weight of the dermatological composition. Preferably, the compound will range from about 0.001 to about 50% by weight of total dermatological composition, more preferably from about 0.1 to about 30% by weight of the composition.

In one embodiment, the application of the present compounds for stimulation of hair growth finds applications in mammalian species, including both humans and animals. In humans, the compounds described herein can be applied for example, to the scalp, face beard, head, pubic area, upper lip, eyebrows, and eyelids. In animal raised for their pelts, e.g., mink, the compounds described herein can be applied over the entire surface of the body to improve the overall pelt for commercial reasons. The process can also be used for cosmetic reasons in animals, e.g., applied to the skin of dogs and cats having bald patches due to mange or other diseases causing a degree of alopecia.

The pharmaceutical compositions contemplated for the stimulation of hair growth include pharmaceutical compositions suited for topical and local action. The term "topical" as employed herein relates to the use of a compound, as described herein, incorporated in a suitable pharmaceutical carrier, and applied at the site of thinning hair or baldness for exertion of local action. Accordingly, such topical compositions include those pharmaceutical forms in which the compound is applied externally by direct contact with the skin to be treated. Conventional pharmaceutical forms for this purpose include ointments, liniments, creams, shampoos, lotions, pastes, jellies, sprays, aerosols, and the like, and may be applied in patches or impregnated dressings depending on the part of the body to be treated. The term "ointment" embraces formulations (including creams) having oleaginous, water-soluble and emulsion-type bases, e.g., petrolatum, lanolin, polyethylene glycols, as well as mixtures of these.

Typically, the compounds can be applied repeatedly for the sustained period of time topically on the part of the body to be treated, for example, the eyelids, eyebrows, skin or scalp. The preferred dosage regimen will generally involve regular, such as daily, administration for a period of treatment of at least one month, more preferably at least three months, and most preferably, at least six months.

For topical use on the eyelids or eyebrows, the active compounds can be formulated in aqueous solutions, creams, ointments, or oils exhibiting physiological acceptable osmolarity by addition of pharmaceutically acceptable buffers and salts. such formulations may or may not, depending on the dispenser, contain preservatives such as benzalkonium chloride, chlorhexidine, chlorobutanol, parahydroxybenzoic acids and phenylmercuric salts such as nitrate, chloride, acetate, and borate, or antioxidants, as well as additives like EDTA, sorbitol, boric acid and the like as additives. Furthermore, particularly aqueous solutions may contain viscosity increasing agents such as polysaccharides, e.g., methylcellulose, mucopolysaccharides, e.g., hyaluronic acid and chondroitin sulfate, or poly alcohol, e.g., polyvinylalcohol. Various slow releasing gels and matrices may also be employed as well as soluble and insoluble ocular inserts, for instance, based on substances forming in situ gels. Depending on the actual formation and compound to be used, various amounts of the drug and different dose regimens may be employed. Typically, the daily amount of compound for treatment of the eyelid may be about 0.1 ng to about 100 mg per eyelid.

For topical use on the skin and scalp, the compound can be advantageously formulated using ointments, creams, liniments or patches as a carrier of the active ingredient. Also, these formulations may or may not contain preservatives, depending on the dispenser and nature of use. Such preservatives include those mentioned above, and methyl-, propyl-, or butyl-parahydroxybenzoic acid, betain, chlorhexidine, benzalkonium chloride, and the like. Various matrices for the slow release delivery may also be used. Typically, the dose to be applied on the scalp is in the range of about 0.1 ng to about 100 mg per day, more preferably about 1 ng to about 10 mg per day, and most preferably about 10 ng to about 1 mg per day depending on the compound and the formulation. To achieve the daily amount of medication depending on the formulation, the compound may be administered once or several times daily with or without anti oxidants.

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

The compounds disclosed herein are also useful in combination with other drugs useful for the treatment of glaucoma or other conditions.

For the treatment of glaucoma, combination treatment with the following classes of drugs are contemplated:

β-Blockers (or β-adrenergic antagonists) including carteolol, levobunolol, metiparanolol, timolol hemihydrate, timolol maleate, β1-selective antagonists such as betaxolol, and the like, or pharmaceutically acceptable salts or prodrugs thereof;

Adrenergic Agonists including non-selective adrenergic agonists such as epinephrine borate, epinephrine hydrochloride, and dipivefrin, and the like, or pharmaceutically acceptable salts or prodrugs thereof; and $α_2$-selective adrenergic agonists such as apraclonidine, brimonidine, and the like, or pharmaceutically acceptable salts or prodrugs thereof;

Carbonic Anhydrase Inhibitors including acetazolamide, dichlorphenamide, methazolamide, brinzolamide, dorzolamide, and the like, or pharmaceutically acceptable salts or prodrugs thereof;

Cholinergic Agonists including direct acting cholinergic agonists such as carbachol, pilocarpine hydrochloride, pilocarbine nitrate, pilocarpine, and the like, or pharmaceutically acceptable salts or prodrugs thereof;

cholinesterase inhibitors such as demecarium, echothiophate, physostigmine, and the like, or pharmaceutically acceptable salts or prodrugs thereof;

Glutamate Antagonists and other neuroprotective agents such as $Ca^{2+}$ channel blockers such as memantine, amantadine, rimantadine, nitroglycerin, dextrophan, dextromethorphan, CGS-19755, dihydropyridines, verapamil, emopamil, benzothiazepines, bepridil, diphenylbutylpiperidines, diphenylpiperazines, HOE 166 and related drugs, fluspirilene, eliprodil, ifenprodil, CP-101,606, tibalosine, 2309BT, and 840S, flunarizine, nicardipine, nifedipine, nimodipine, barnidipine, verapamil, lidoflazine, prenylamine lactate, amiloride, and the like, or pharmaceutically acceptable salts or prodrugs thereof;

Prostamides such as bimatoprost, or pharmaceutically acceptable salts or prodrugs thereof; and Prostaglandins including travoprost, UFO-21, chlorprostenol, fluprostenol, 13,14-dihydro-chlorprostenol, isopropyl unoprostone, latanoprost and the like.

Cannabinoids including CB1 agonists such as WIN-55212-2 and CP-55940 and the like, or pharmaceutically acceptable salts or prodrugs thereof.

For treatment of diseases affecting the eye including glaucoma, these compounds can be administered topically, periocularly, intraocularly, or by any other effective means known in the art.

Treatment of inflammatory bowel disease may be accomplished by the administration of the compounds described herein to the suffering mammal. Inflammatory bowel disease describes a variety of diseases characterized by inflammation of the bowels including, but not limited to, ulcerative colitis and Crohn's disease. Treatment may be accomplished by oral administration, by suppository, or parenteral administration, or some other suitable method.

While not intending to limit the scope of the invention in any way, delivery of the compounds disclosed herein to the colon via oral dosage forms may be accomplished by any of a number of methods known in the art. For example, reviews by Chourasia and Jain in J Pharm Pharmaceut Sci 6 (1): 33-66, 2003 and Shareef et. al (AAPS PharmSci 2003; 5 (2) Article 17) describe a number of useful methods. While not intending to limit the scope of the invention in any way these methods include 1) administration of a prodrug, including an azo or a carbohydrate based prodrug; 2) coating the drug with, or encapsulating or impregnating the drug into a polymer designed for delivery to the colon, 3) time released delivery of the drug, 4) use of a bioadhesive system; and the like.

While not intending to be bound in any way by theory, it is believed that intestinal microflora are capable of reductive cleavage of an azo bond leaving the two nitrogen atoms as amine functional groups. While not intending to limit the scope of the invention in any way, the azo prodrug approach has been used to deliver to 5-aminosalicylic acid to the colons of humans in clinical trials for the treatment of inflammatory bowel disease. It is also believed that bacteria of the lower GI also have enzymes which can digest glycosides, glucuronides, cyclodextrins, dextrans, and other carbohydrates, and ester prodrugs formed from these carbohydrates have been shown to deliver the parent active drugs selectively to the colon. For example, in vivo and in vitro studies on rats and guinea pigs with prodrugs of dexamethasone, prednisolone, hydrocortisone, and fludrocortisone, suggest that glycoside conjugates may be useful for the delivery of steroids to the human colon. Other in vivo studies have suggested that glucouronide, cyclodextrin, and dextran prodrugs of steroids or non-steroidal anti-inflammatory drugs are useful for delivery of these drugs to the lower GI tract. An amide of salicylic acid and glutamic acid has been shown to be useful for the delivery of salicylic acid to the colon of rabbit and dog.

While not intending to limit the scope of the invention in any way, carbohydrate polymers such as amylase, arabinogalactan, chitosan, chondroitin sulfate, dextran, guar gum, pectin, xylin, and the like, or azo-group containing polymers can be used to coat a drug compound, or a drug may be impregnated or encapsulated in the polymer. It is believed that after oral administration, the polymers remain stable in the upper GI tract, but are digested by the microflora of the lower GI thus releasing the drug for treatment.

Polymers which are sensitive to pH may also be used since the colon has a higher pH than the upper GI tract. Such polymers are commercially available. For example, Rohm Pharmaceuticals, Darmstadt, Germany, markets pH dependent methacrylate based polymers and copolymers which have varying solubilities over different pH ranges based upon the number of free carboxylate groups in the polymer under the tradename Eudragit®. Several Eudragit® dosage forms are currently used to deliver salsalazine for the treatment of ulcerative colitis and Crohn's disease. Time release systems, bioadhesive systems, and other delivery systems have also been studied.

One embodiment is use of a compound in the manufacture of a medicament for the treatment of inflammatory bowel disease, said compound comprising

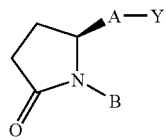

or a pharmaceutically acceptable salt thereof, or a prodrug thereof;
wherein Y is

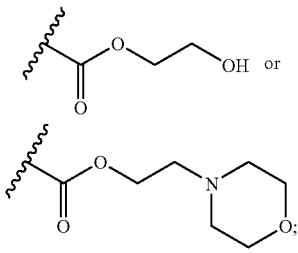

A is —$(CH_2)_6$—, cis —$CH_2CH=CH$—$(CH_2)_3$—, or —$CH_2C\equiv C$—$(CH_2)_3$—, wherein 1 or 2 carbon atoms may be substituted with S or O; or A is —$(CH_2)_m$—Ar—$(CH_2)_o$— wherein Ar is interarylene or heterointerarylene, the sum of m and o is from 1 to 4, and wherein one $CH_2$ may be substituted with S or O; and B is aryl or heteroaryl.

Another embodiment is use of a compound in the manufacture of a medicament for the treatment of inflammatory bowel disease, said compound comprising

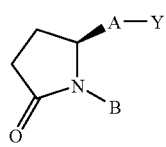

or a pharmaceutically acceptable salt thereof, or a prodrug thereof;
wherein Y is

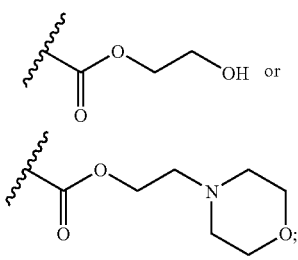

A is —$(CH_2)_6$—, cis —$CH_2CH=CH$—$(CH_2)_3$—, or —$CH_2C\equiv C$—$(CH_2)_3$—, wherein 1 or 2 carbon atoms may be substituted with S or O; or A is —$(CH_2)_m$—Ar—$(CH_2)_o$— wherein Ar is interarylene or heterointerarylene, the sum of m and o is from 1 to 4, and wherein one $CH_2$ may be substituted with S or O; and B is phenyl.

Another embodiment is use of a compound in the manufacture of a medicament for the treatment of inflammatory bowel disease, said compound comprising

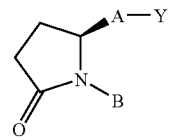

or a pharmaceutically acceptable salt thereof, or a prodrug thereof;
wherein Y is

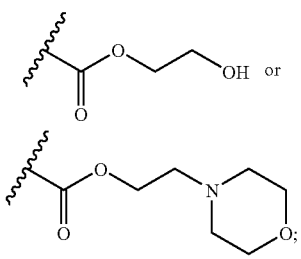

A is —$(CH_2)_6$—, cis —$CH_2CH=CH$—$(CH_2)_3$—, or —$CH_2C\equiv C$—$(CH_2)_3$—, wherein 1 or 2 carbon atoms may be substituted with S or O; or A is —$(CH_2)_m$—Ar—$(CH_2)_o$— wherein Ar is interarylene or heterointerarylene, the sum of m and o is from 1 to 4, and wherein one $CH_2$ may be substituted with S or O; and B is alkylphenyl.

Another embodiment is use of a compound in the manufacture of a medicament for the treatment of inflammatory bowel disease, said compound comprising

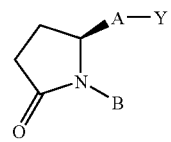

or a pharmaceutically acceptable salt thereof, or a prodrug thereof;
wherein Y is

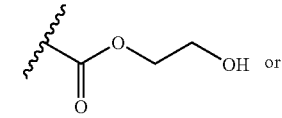

-continued

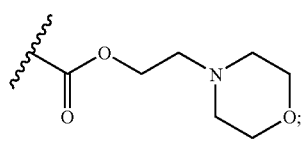

A is —(CH₂)₆—, cis —CH₂CH═CH—(CH₂)₃—, or —CH₂C≡C—(CH₂)₃—, wherein 1 or 2 carbon atoms may be substituted with S or O; or A is —(CH₂)ₘ—Ar—(CH₂)ₒ— wherein Ar is interarylene or heterointerarylene, the sum of m and o is from 1 to 4, and wherein one CH₂ may be substituted with S or O; and
B is p-t-butylphenyl.

Another embodiment is use of a compound in the manufacture of a medicament for the treatment of inflammatory bowel disease, said compound of comprising

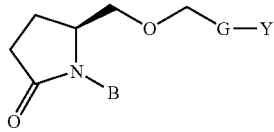

or a pharmaceutically acceptable salt thereof, or a prodrug thereof;
wherein Y is

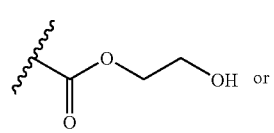

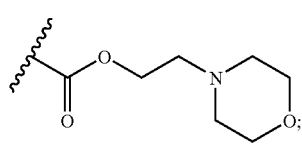

G is 1,3-interaryl or interheteroaryl, or —(CH₂)₃—; and
B is aryl or heteroaryl.

Another embodiment is use of a compound in the manufacture of a medicament for the treatment of inflammatory bowel disease, said compound of comprising

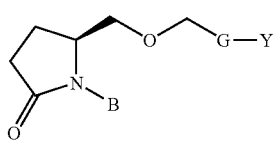

or a pharmaceutically acceptable salt thereof, or a prodrug thereof;
wherein Y is

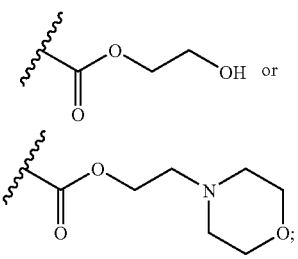

G is 1,3-interaryl or interheteroaryl, or —(CH₂)₃—; and
B is phenyl.

Another embodiment is use of a compound in the manufacture of a medicament for the treatment of inflammatory bowel disease, said compound of comprising

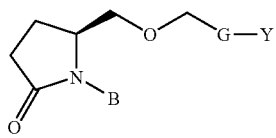

or a pharmaceutically acceptable salt thereof, or a prodrug thereof;
wherein Y is

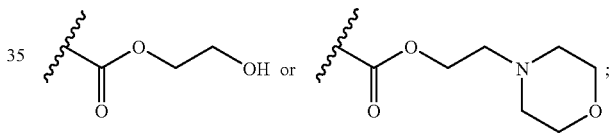

G is 1,3-interaryl or interheteroaryl, or —(CH₂)₃—; and
B is hydroxyalkylphenyl.

Another embodiment is use of a compound in the manufacture of a medicament for the treatment of inflammatory bowel disease, said compound comprising

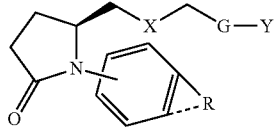

or a pharmaceutically acceptable salt thereof, or a prodrug thereof;
wherein a dashed line indicates the presence or absence of a bond;
Y is

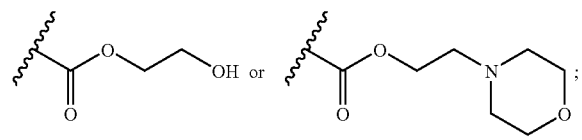

R is hydrocarbyl or hydroxyhydrocarbyl having from 1 to 12 carbon atoms;
X is $CH_2$, O, or S; and
G is 1,3-interaryl or interheteroaryl, or —$(CH_2)_3$—.

Another embodiment is use of a compound in the manufacture of a medicament for the treatment of inflammatory bowel disease, said compound comprising an N-aryl or N-heteroaryl gamma lactam which is effective at reducing intraocular pressure in a mammal.

One embodiment is use of a compound in the manufacture of a medicament for the treatment of baldness, said compound comprising

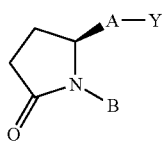

or a pharmaceutically acceptable salt thereof, or a prodrug thereof;
wherein Y is

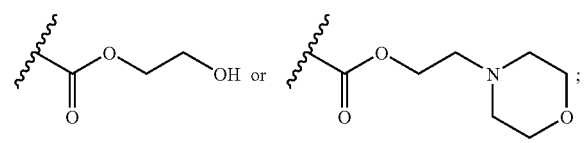

A is —$(CH_2)_6$—, cis —$CH_2CH$=$CH$—$(CH_2)_3$—, or —$CH_2C$≡$C$—$(CH_2)_3$—, wherein 1 or 2 carbon atoms may be substituted with S or O; or A is —$(CH_2)_m$—Ar—$(CH_2)_o$— wherein Ar is interarylene or heterointerarylene, the sum of m and o is from 1 to 4, and wherein one $CH_2$ may be substituted with S or O; and
B is aryl or heteroaryl.

Another embodiment is use of a compound in the manufacture of a medicament for the treatment of baldness, said compound comprising

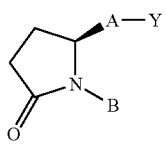

or a pharmaceutically acceptable salt thereof, or a prodrug thereof;
wherein Y is

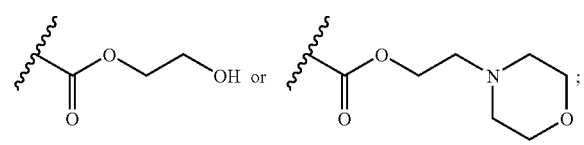

A is —$(CH_2)_6$—, cis —$CH_2CH$=$CH$—$(CH_2)_3$—, or —$CH_2C$≡$C$—$(CH_2)_3$—, wherein 1 or 2 carbon atoms may be substituted with S or O; or A is —$(CH_2)_m$—Ar—$(CH_2)_o$— wherein Ar is interarylene or heterointerarylene, the sum of m and o is from 1 to 4, and wherein one $CH_2$ may be substituted with S or O; and
B is phenyl.

Another embodiment is use of a compound in the manufacture of a medicament for the treatment of baldness, said compound comprising

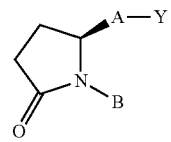

or a pharmaceutically acceptable salt thereof, or a prodrug thereof;
wherein Y is

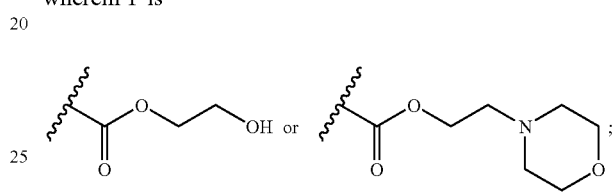

A is —$(CH_2)_6$—, cis —$CH_2CH$=$CH$—$(CH_2)_3$—, or —$CH_2C$≡$C$—$(CH_2)_3$—, wherein 1 or 2 carbon atoms may be substituted with S or O; or A is —$(CH_2)_m$—Ar—$(CH_2)_o$— wherein Ar is interarylene or heterointerarylene, the sum of m and o is from 1 to 4, and wherein one $CH_2$ may be substituted with S or O; and
B is alkylphenyl.

Another embodiment is use of a compound in the manufacture of a medicament for the treatment of baldness, said compound comprising

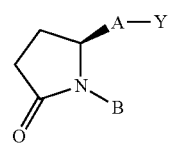

or a pharmaceutically acceptable salt thereof, or a prodrug thereof;
wherein Y is

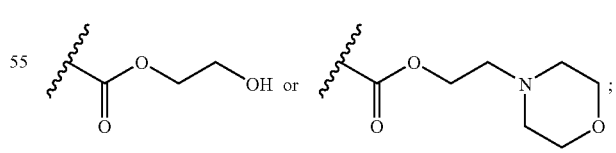

A is —$(CH_2)_6$—, cis —$CH_2CH$=$CH$—$(CH_2)_3$—, or —$CH_2C$≡$C$—$(CH_2)_3$—, wherein 1 or 2 carbon atoms may be substituted with S or O; or A is —$(CH_2)_m$—Ar—$(CH_2)_o$— wherein Ar is interarylene or heterointerarylene, the sum of m and o is from 1 to 4, and wherein one $CH_2$ may be substituted with S or O; and
B is p-t-butylphenyl.

Another embodiment is use of a compound in the manufacture of a medicament for the treatment of baldness, said compound of comprising

[structure: pyrrolidinone with CH2-O-CH2-G-Y substituent and N-B]

or a pharmaceutically acceptable salt thereof, or a prodrug thereof;
wherein Y is

[structures: -C(=O)-O-CH2CH2-OH or -C(=O)-O-CH2CH2-N-morpholine];

G is 1,3-interaryl or interheteroaryl, or —(CH₂)₃—; and
B is aryl or heteroaryl.

Another embodiment is use of a compound in the manufacture of a medicament for the treatment of baldness, said compound of comprising

[structure: pyrrolidinone with CH2-O-CH2-G-Y, N-B]

or a pharmaceutically acceptable salt thereof, or a prodrug thereof;
wherein Y is

[structures: -C(=O)-O-CH2CH2-OH or -C(=O)-O-CH2CH2-N-morpholine];

G is 1,3-interaryl or interheteroaryl, or —(CH₂)₃—; and
B is phenyl.

Another embodiment is use of a compound in the manufacture of a medicament for the treatment of baldness, said compound of comprising

[structure: pyrrolidinone with CH2-O-CH2-G-Y, N-B]

or a pharmaceutically acceptable salt thereof, or a prodrug thereof;
wherein Y is

[structures: -C(=O)-O-CH2CH2-OH or -C(=O)-O-CH2CH2-N-morpholine];

G is 1,3-interaryl or interheteroaryl, or —(CH₂)₃—; and
B is hydroxyalkylphenyl.

Another embodiment is use of a compound in the manufacture of a medicament for the treatment of baldness, said compound comprising

[structure: pyrrolidinone with CH2-X-CH2-G-Y, N attached to aryl with R]

or a pharmaceutically acceptable salt thereof, or a prodrug thereof;
wherein a dashed line indicates the presence or absence of a bond;
Y is

[structures: -C(=O)-O-CH2CH2-OH or -C(=O)-O-CH2CH2-N-morpholine];

R is hydrocarbyl or hydroxyhydrocarbyl having from 1 to 12 carbon atoms;
X is CH₂, O, or S; and
G is 1,3-interaryl or interheteroaryl, or —(CH₂)₃—.

Another embodiment is use of a compound in the manufacture of a medicament for the treatment of baldness, said compound comprising an N-aryl or N-heteroaryl gamma lactam which is effective at reducing intraocular pressure in a mammal.

One embodiment is a compound comprising

[structure: pyrrolidinone with A-Y and N-B]

or a pharmaceutically acceptable salt thereof, or a prodrug thereof;
wherein Y is

[structures: -C(=O)-O-CH2CH2-OH or -C(=O)-O-CH2CH2-N-morpholine];

A is —(CH$_2$)$_6$—, cis —CH$_2$CH═CH—(CH$_2$)$_3$—, or —CH$_2$C≡C—(CH$_2$)$_3$—, wherein 1 or 2 carbon atoms may be substituted with S or O; or A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O; and B is aryl or heteroaryl.

Another embodiment is a compound comprising

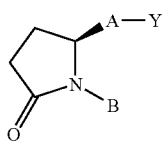

or a pharmaceutically acceptable salt thereof, or a prodrug thereof;

wherein Y is

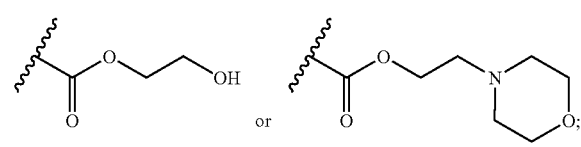

A is —(CH$_2$)$_6$—, cis —CH$_2$CH═CH—(CH$_2$)$_3$—, or —CH$_2$C≡C—(CH$_2$)$_3$—, wherein 1 or 2 carbon atoms may be substituted with S or O; or A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O; and B is phenyl.

Another embodiment is a compound comprising

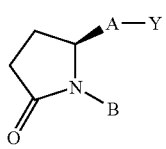

or a pharmaceutically acceptable salt thereof, or a prodrug thereof;

wherein Y is

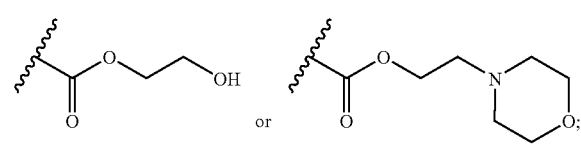

A is —(CH$_2$)$_6$—, cis —CH$_2$CH═CH—(CH$_2$)$_3$—, or —CH$_2$C≡C—(CH$_2$)$_3$—, wherein 1 or 2 carbon atoms may be substituted with S or O; or A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O; and B is alkylphenyl.

Another embodiment is a compound comprising

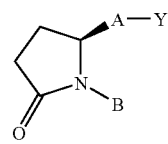

or a pharmaceutically acceptable salt thereof, or a prodrug thereof;

wherein Y is

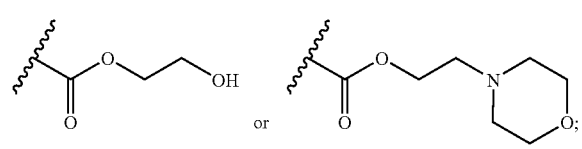

A is —(CH$_2$)$_6$—, cis —CH$_2$CH═CH—(CH$_2$)$_3$—, or —CH$_2$C≡C—(CH$_2$)$_3$—, wherein 1 or 2 carbon atoms may be substituted with S or O; or A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O; and B is p-t-butylphenyl.

Another embodiment is a compound of comprising

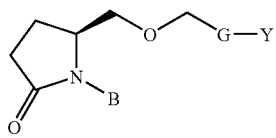

or a pharmaceutically acceptable salt thereof, or a prodrug thereof;

wherein Y is

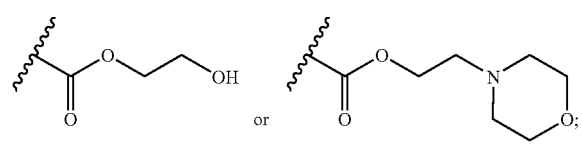

G is 1,3-interaryl or interheteroaryl, or —(CH$_2$)$_3$—; and

B is aryl or heteroaryl.

Another embodiment is a compound of comprising

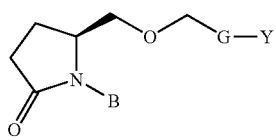

or a pharmaceutically acceptable salt thereof, or a prodrug thereof;

wherein Y is

![structures: two Y groups - ester-O-CH2CH2-OH and ester-O-CH2CH2-morpholine]

G is 1,3-interaryl or interheteroaryl, or —(CH$_2$)$_3$—; and
B is phenyl.

Another embodiment is a compound of comprising

![pyrrolidinone structure with O-CH2-G-Y substituent and N-B]

or a pharmaceutically acceptable salt thereof, or a prodrug thereof;
wherein Y is ![two Y groups - ester-O-CH2CH2-OH and ester-O-CH2CH2-morpholine]

G is 1,3-interaryl or interheteroaryl, or —(CH$_2$)$_3$—; and
B is hydroxyalkylphenyl.

Another embodiment is a compound comprising

![pyrrolidinone structure with X-CH2-G-Y and N-aryl with R]

or a pharmaceutically acceptable salt thereof, or a prodrug thereof;
wherein a dashed line indicates the presence or absence of a bond;
Y is ![two Y groups - ester-O-CH2CH2-OH and ester-O-CH2CH2-morpholine]

R is hydrocarbyl or hydroxyhydrocarbyl having from 1 to 12 carbon atoms;
X is CH$_2$, O, or S; and
G is 1,3-interaryl or interheteroaryl, or —(CH$_2$)$_3$—.

Another embodiment is a compound comprising an N-aryl or N-heteroaryl gamma lactam which is effective at reducing intraocular pressure in a mammal.

Embodiments contemplated for each compound disclosed herein are use of the compound in the manufacture of a medicament for the treatment of glaucoma or ocular hypertension.

Embodiments contemplated for each compound disclosed herein are use of the compound in the manufacture of a medicament for the treatment of inflammatory bowel disease.

Embodiments contemplated for each compound disclosed herein are use of the compound in the manufacture of a medicament for the treatment of baldness.

Embodiments contemplated for each compound disclosed herein are methods comprising administering an effective amount of the compound to a mammal for the treatment of glaucoma or ocular hypertension.

Embodiments contemplated for each compound disclosed herein are methods comprising administering an effective amount of the compound to a mammal for the treatment of inflammatory bowel disease.

Embodiments contemplated for each compound disclosed herein are methods comprising administering an effective amount of the compound to a mammal for the treatment of baldness.

Embodiments contemplated for each compound disclosed herein are compositions comprising the compound, wherein said compositions are ophthalmically acceptable liquids.

EXAMPLE 1

The compounds disclosed herein may be prepared from the compound shown below using the procedures described in U.S. Provisional Patent Application No. 60/660,748, filed Mar. 10, 2005, the disclosure of which is expressly incorporated by reference herein, and in U.S. Provisional Patent Application No. 60/022,172, filed Jan. 18, 2008. Unless stereochemistry is explicitly depicted, a structure is intended to include every possible stereoisomer, both pure or in any possible mixture.

![Compound 1: pyrrolidinone with N-phenyl(CH(OH)butyl) and propyl-thiophene-2-carbonyl chloride]

1. ClCO$_2$Et, Et$_3$N, CH$_2$Cl$_2$
2. RCH$_2$CH$_2$OH
→

![Compound 2: analogous ester product with OR group]

2
a R = OH
b R = morpholinyl-ethyl

Compound 2a

Triethylamine and ethyl chloroformate are added sequentially to a solution of compound 1 in CH$_2$Cl$_2$ at room temperature. After 2.5 h, triethylamine and ethylene glycol are added. After stirring overnight at room temperature, the reaction mixture is partitioned between H$_2$O and CH$_2$Cl$_2$. The phases are separated and the aqueous phase is extracted with CH$_2$Cl$_2$ (2×). The combined organic phase is washed with 1 N HCl then dried (MgSO$_4$), filtered and concentrated in vacuo. Purification of the residue by flash column chromatography on silica gel (10% CH$_3$OH/CH$_2$Cl$_2$) affords compound 2a.

Compound 2b

Triethylamine and ethyl chloroformate are added sequentially to a solution of compound 1 in CH$_2$Cl$_2$ at room temperature. After 2.5 h, triethylamine and 4-(2-hydroxyethyl)-morphine are added. After stirring overnight at room temperature, the reaction mixture is partitioned between H$_2$O and CH$_2$Cl$_2$. The phases are separated and the aqueous phase is extracted with CH$_2$Cl$_2$ (2×). The combined organic phase is washed with 1 N HCl then dried (MgSO$_4$), filtered and concentrated in vacuo. Purification of the residue by flash column chromatography on silica gel (10% CH$_3$OH/CH$_2$Cl$_2$) affords compound 2b.

The compounds disclosed below are hypothetical examples of compound which are useful as described herein. Each of these compounds, and salts thereof, and prodrugs thereof, are specifically contemplated as individual embodiments.

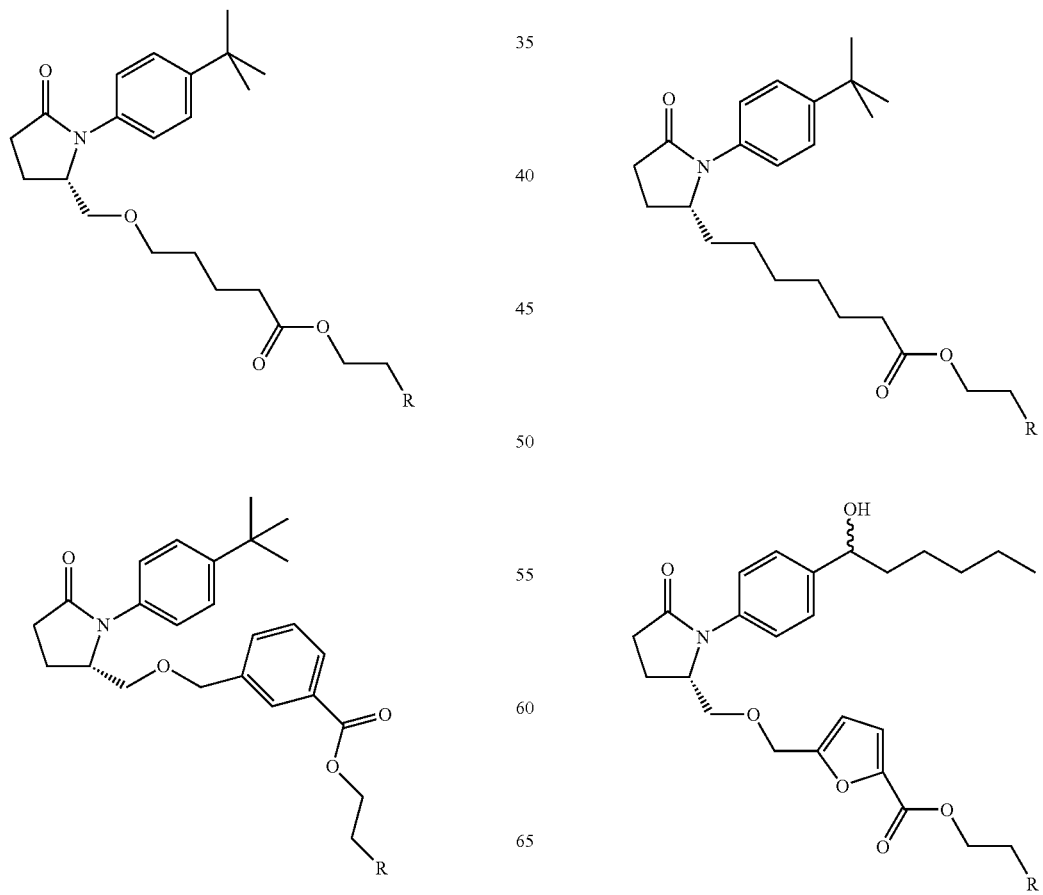

-continued

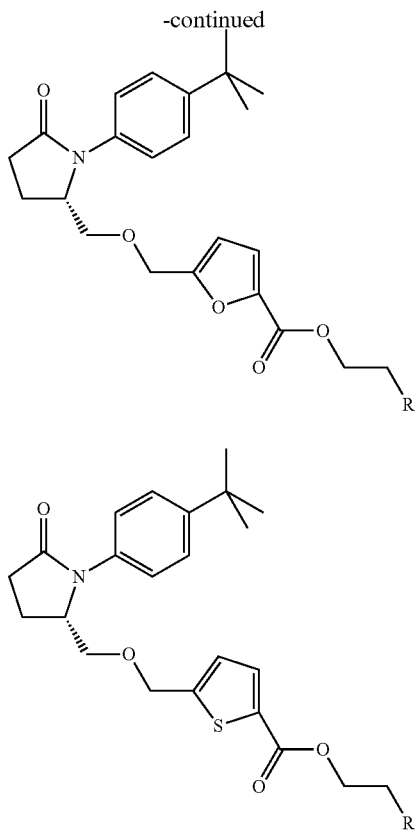

43 44
-continued -continued
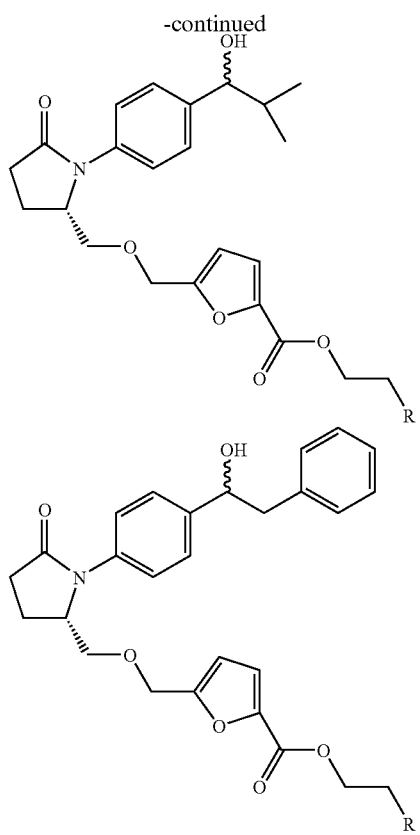
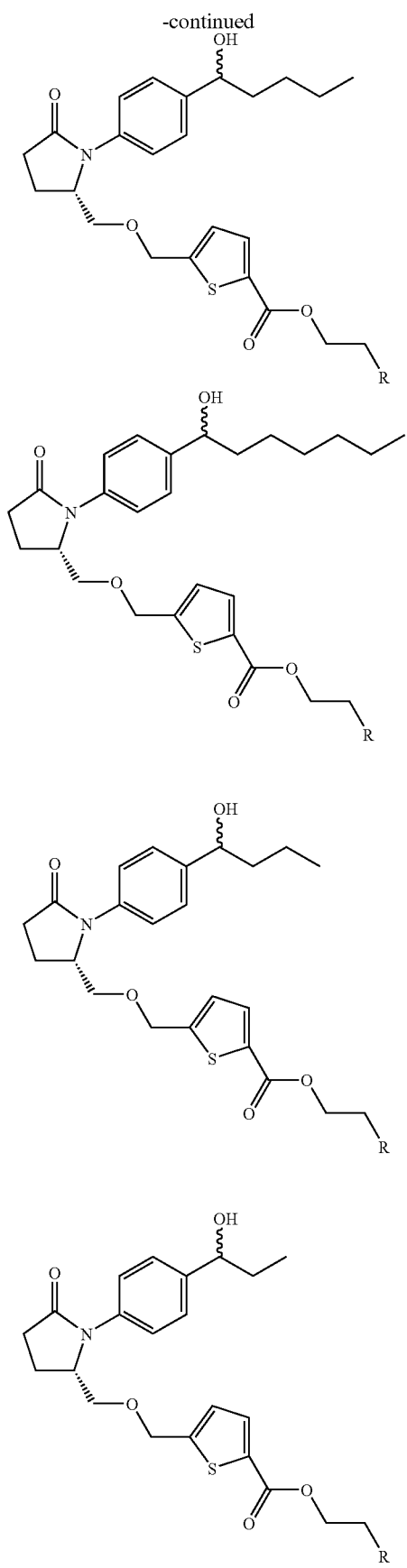

-continued
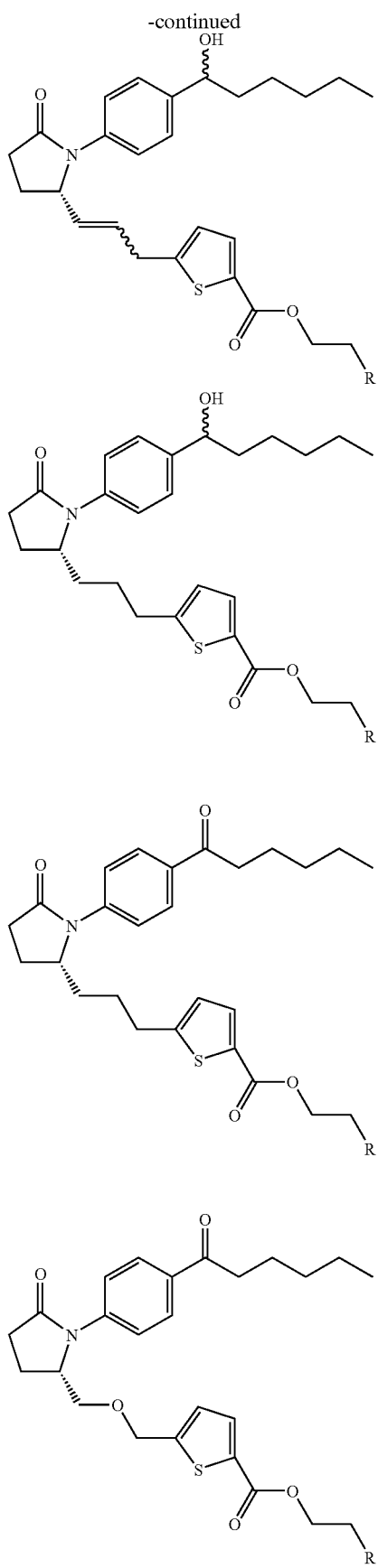
-continued
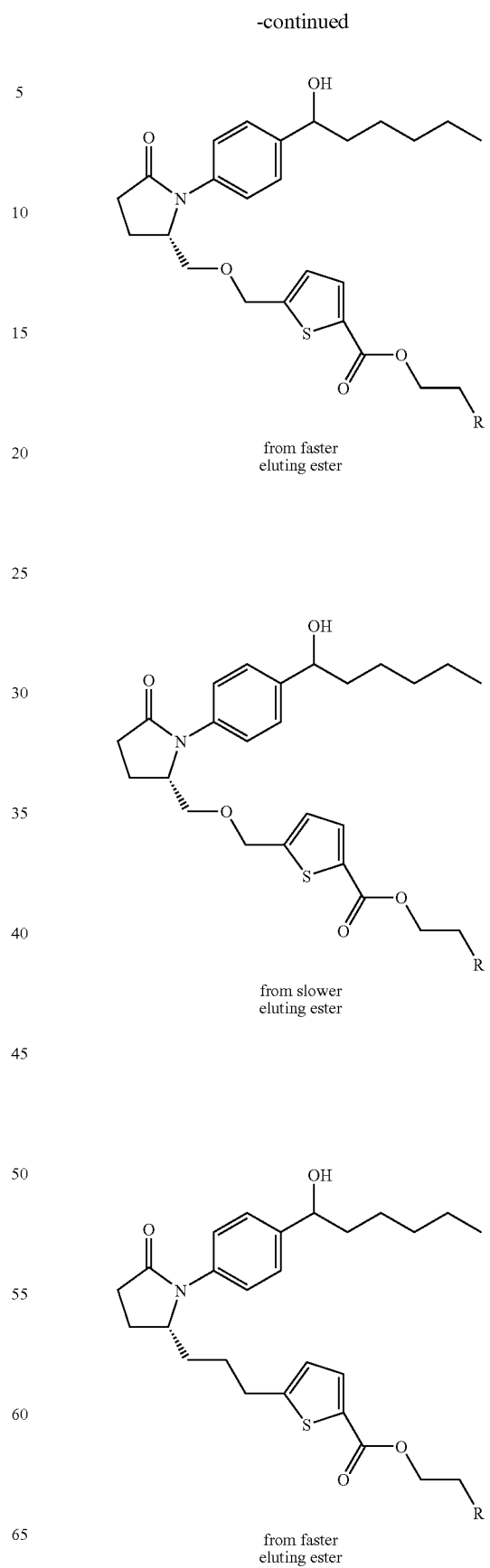
from faster
eluting ester
from slower
eluting ester
from faster
eluting ester -continued
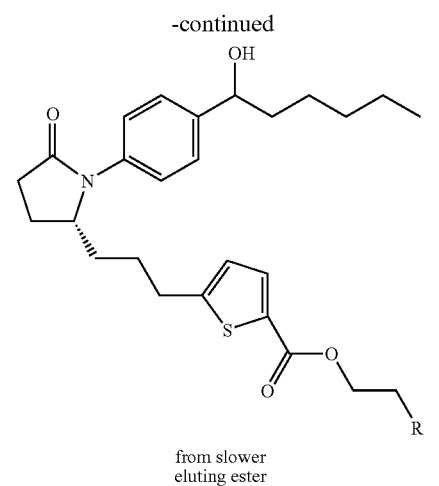
from slower
eluting ester
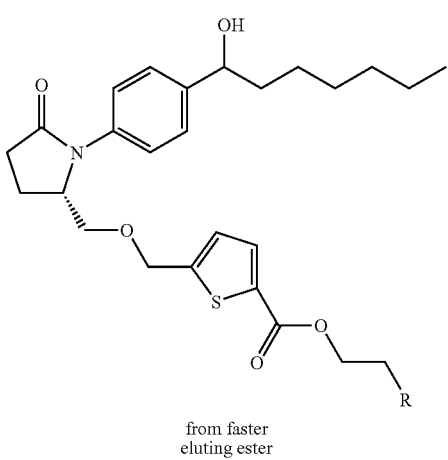
from faster
eluting ester
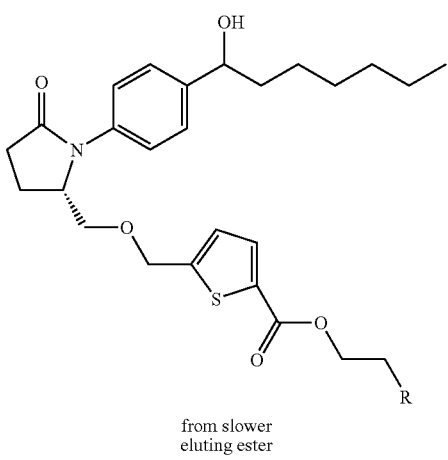
from slower
eluting ester
-continued
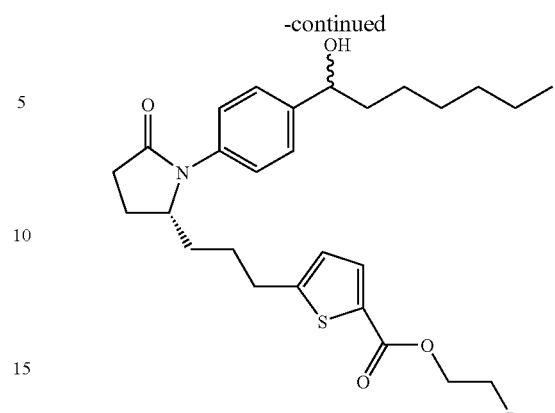
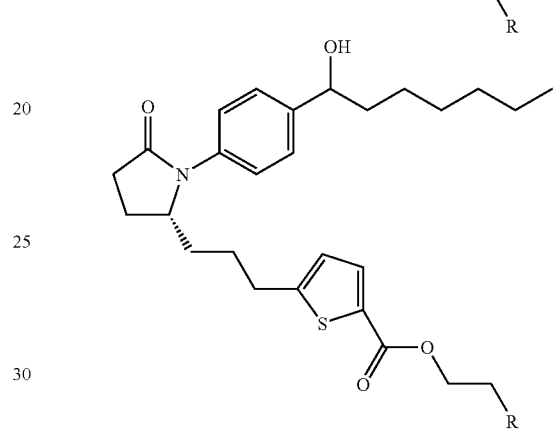
from faster
eluting ester
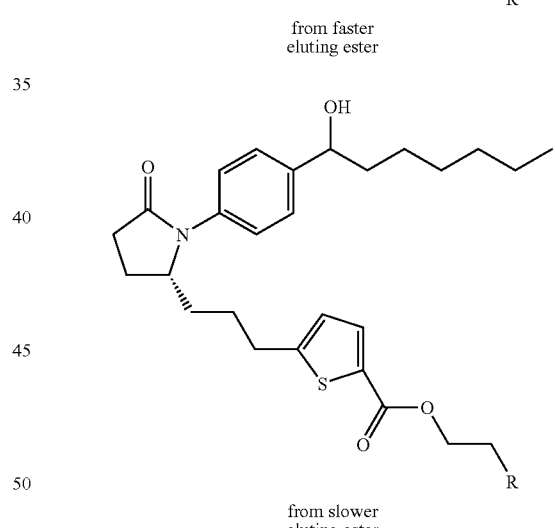
from slower
eluting ester
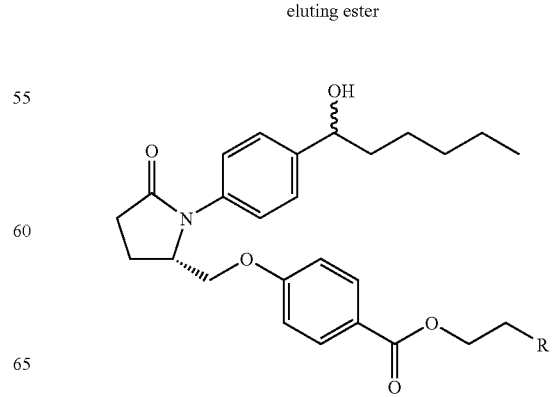

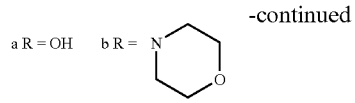

Running binding and activity studies on the hypothetical compounds above as described in U.S. Provisional Patent Application No. 60/660,748 would demonstrate that the compounds disclosed herein are selective prostaglandin $EP_2$ agonists, and are thus useful for the treatment of glaucoma, ocular hypertension, inflammatory bowel disease, and the other diseases or conditions disclosed herein.

IN VIVO EXAMPLES

Compounds such as those described in the above are tested in vivo to measure its ability to reduce intraocular pressure. Compound 2a is tested in normotensive dogs. The intraocular pressure (IOP) decreases from baseline. This compound is also tested in laser-induced hypertensive monkeys, the IOP decreases from baseline.

Compound 2b is tested in normotensive dogs. The intraocular pressure (IOP) decreases from baseline. This compound is also tested in laser-induced hypertensive monkeys, the IOP decreases from baseline.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

What is claimed is:

1. A compound of the formula

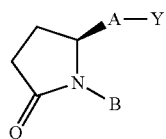

or a pharmaceutically acceptable salt thereof, or a prodrug thereof;
wherein
Y is

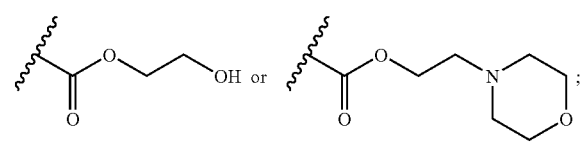

A is —$(CH_2)_6$—, cis —$CH_2CH$=$CH$—$(CH_2)_3$—, or —$CH_2C$≡$C$—$(CH_2)_3$—, wherein 1 or 2 carbon atoms may be substituted with S or O; or A is —$(CH_2)_m$—Ar—$(CH_2)_o$— wherein Ar is interarylene or heterointerarylene, the sum of m and o is from 1 to 4, and wherein one $CH_2$ may be substituted with S or O; and B is aryl or heteroaryl.

2. The compound of claim 1 wherein A has a structure selected from

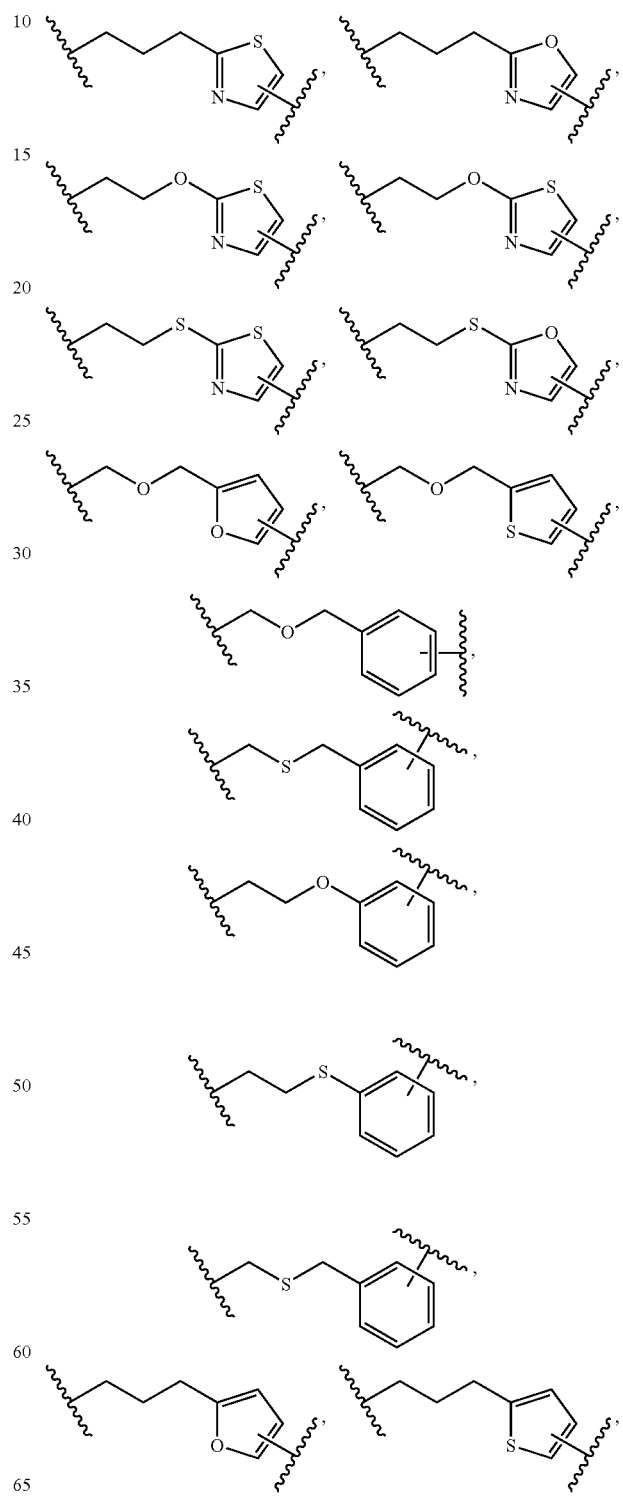

-continued

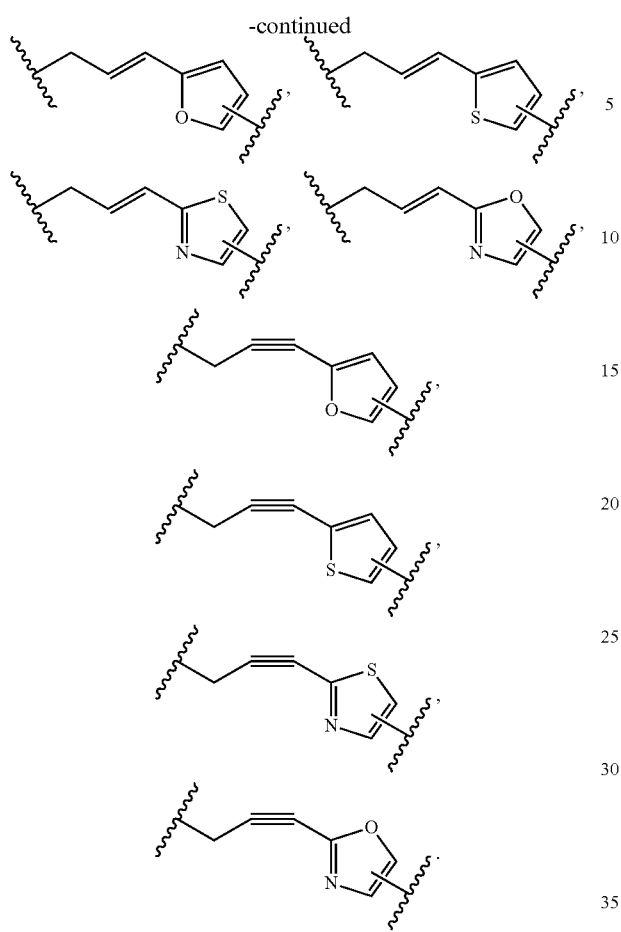

3. The compound of claim 2 wherein A is 5-(3-propyl)thiophen-2-yl.
4. The compound of claim 1 wherein A is 6-hexyl.
5. The compound of claim 1 wherein A is (Z)-6-hex-4-enyl.
6. The compound of claim 1 wherein B is substituted phenyl.
7. The compound of claim 1 having the structure

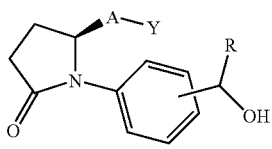

or a pharmaceutically acceptable salt thereof, or a prodrug thereof, wherein R is hydrogen or $C_{1-10}$ hydrocarbyl.
8. The compound of claim 7 having the structure

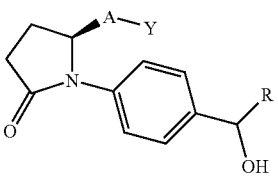

or a pharmaceutically acceptable salt thereof, or a prodrug thereof, wherein R is hydrogen or $C_{1-10}$ hydrocarbyl.
9. The compound of claim 1 of the formula

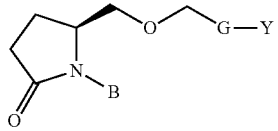

or a pharmaceutically acceptable salt thereof, or a prodrug thereof;
    wherein G is 1,3-interaryl or interheteroaryl, or —(CH$_2$)$_3$—.
10. The compound of claim 1 of the formula

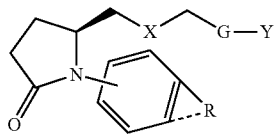

or a pharmaceutically acceptable salt thereof, or a prodrug thereof;
    wherein a dashed line indicates the presence or absence of a bond;
    R is hydrocarbyl or hydroxyhydrocarbyl having from 1 to 12 carbon atoms;
    X is CH$_2$, O, or S; and
    G is 1,3-interaryl or interheteroaryl, or —(CH$_2$)$_3$—.
11. The compound of claim 4 of the formula

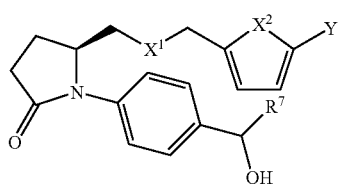

or a pharmaceutically acceptable salt thereof, or a prodrug thereof,
    wherein $X^1$ and $X^2$ are independently CH, O, or S; and
    $R^7$ is linear alkyl comprising from 3 to 7 carbon atoms.
12. The compound of claim 4 of the formula

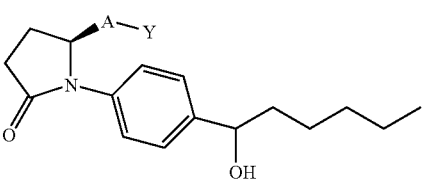

or a pharmaceutically acceptable salt thereof, or a prodrug thereof.

13. The compound of claim 1 of the formula

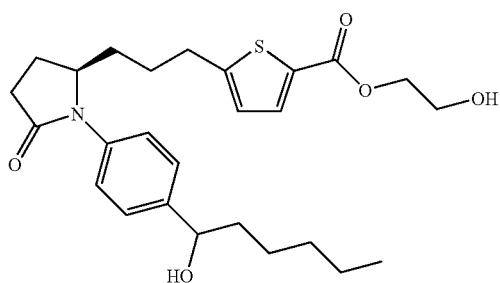

or a pharmaceutically acceptable salt thereof, or a prodrug thereof.

14. The compound of claim 1 of the formula

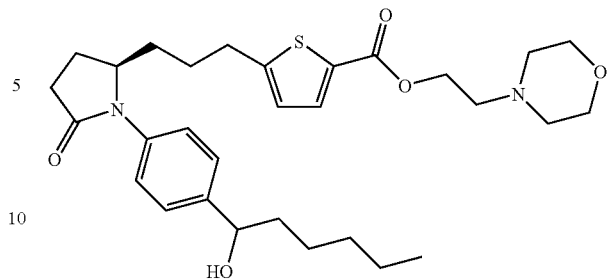

or a pharmaceutically acceptable salt thereof, or a prodrug thereof.

15. A method of treating baldness comprising administering to a subject in need thereof a therapeutically effective amount of a compound according to claim 1.

* * * * *